United States Patent
Ellsworth et al.

(10) Patent No.: US 10,131,942 B2
(45) Date of Patent: Nov. 20, 2018

(54) METHODS FOR TREATING BARRETT'S METAPLASIA AND ESOPHAGEAL ADENOCARCINOMA

(71) Applicant: Interpace Diagnostics Corporation, Parsippany, NJ (US)

(72) Inventors: Eric Matthew Gayle Ellsworth, Pittsburgh, PA (US); Sydney David Finkelstein, Pittsburgh, PA (US); Sara Ann Jackson, Pittsburgh, PA (US); Brendan Corcoran, Pittsburgh, PA (US); Dennis Morgan Smith, Jr., St. Augustine, FL (US)

(73) Assignee: INTERPACE DIAGNOSTICS CORPORATION, Parsippany, NJ (US)

( * ) Notice: Subject to any disclaimer, the term of this patent is extended or adjusted under 35 U.S.C. 154(b) by 106 days.

(21) Appl. No.: 13/954,247

(22) Filed: Jul. 30, 2013

(65) Prior Publication Data

US 2013/0317317 A1  Nov. 28, 2013

Related U.S. Application Data

(63) Continuation-in-part of application No. 13/692,727, filed on Dec. 3, 2012.

(60) Provisional application No. 61/565,879, filed on Dec. 1, 2011, provisional application No. 61/640,527, filed on Apr. 30, 2012, provisional application No. 61/661,256, filed on Jun. 18, 2012.

(51) Int. Cl.
| | |
|---|---|
| *C12Q 1/6869* | (2018.01) |
| *A61N 5/06* | (2006.01) |
| *A61B 18/02* | (2006.01) |
| *A61B 18/12* | (2006.01) |
| *A61B 18/00* | (2006.01) |

(52) U.S. Cl.
CPC ........... *C12Q 1/6869* (2013.01); *A61N 5/062* (2013.01); *A61B 18/02* (2013.01); *A61B 18/12* (2013.01); *A61B 2018/00488* (2013.01); *A61N 2005/0609* (2013.01)

(58) Field of Classification Search
None
See application file for complete search history.

(56) References Cited

U.S. PATENT DOCUMENTS

| | | |
|---|---|---|
| 6,340,563 B1 | 1/2002 | Finkelstein et al. |
| 7,014,999 B2 | 3/2006 | Finkelstein et al. |
| 8,034,577 B2 | 10/2011 | Finkelstein et al. |
| 2006/0088871 A1 | 4/2006 | Finkelstein et al. |
| 2006/0088874 A1 | 4/2006 | Bacher et al. |
| 2013/0143222 A1 | 6/2013 | Ellsworth et al. |
| 2013/0267426 A1 | 10/2013 | Vib Vzw et al. |
| 2014/0296103 A1 | 10/2014 | Finkelstein et al. |

FOREIGN PATENT DOCUMENTS

WO    2002088388    11/2012

OTHER PUBLICATIONS

Daglilar et al. A Preliminary longitudinal assessment of mutational load in patients with Barrett's Esophagus. Presented at DDW 2013, Orange County Convention, Orlando, FL. May 18-21, 2013.

Daglilar et al., Mutational load as a predictor of progression in Barrett's Esophagus: a longitudinal study. ASGE Poster Session No. Tu1307, Presented at Digestive Disease Week®, McCormick Place-South, Chicago, IL, May 3-6, 2014.

Ellsworth et al., Cumulative Mutational Change in Dysplastic and Non-Dysplastic Barrett's Esophagus, AGA Poster Session Tu1113, Presented at Digestive Disease Week®, San Diego Convention Center, San Diego, CA, May 19-22, 2012.

Ellsworth et al., Correlation of the presence and extent of loss of heterozygosity mutations with histological classifications of Barrett's esophagus. BMC Gastroenterol. (Dec 27, 2012), 12:181, pp. 1-10.

Finkelstein et al., Molecular pathogenesis of early development and progression of Barrett's esophagus, Poster M1949, Presented at DDW 2008, May 19, 2008.

Finkelstein et al., The molecular pathology of radiofrequency mucosal ablation of Barrett's esophagus, Poster M1944, Presented at DDW 2008 May 19, 2008.

Khara et al. Evaluation of Mutational Load (ML) in Four Independent Datasets with Dysplastic and Non-Dysplastic; Barrett's Esophagus, Presented at DDW 2013, Orange County Convention, Orlando, FL, May 18-21, 2013.

Khara et al., Assessment of mutational load in biopsy tissue provides additional information about genomic instability to histological classifications of Barrett's esophagus, J. Gastrointest Canc. (2014), 45:137-145.

Meltzer, et al., Microsatellite Instability Occurs Frequently and in Both Diploid and Aneuploid Cell Populations of Barrett's-associated Esophageal Adenocarcinomas, Cancer Research, (Jul. 1, 1994), 54:3379-3382.

Patel et al., Evaluating Mutation Load in Low and High Grade; Dysplasia in Barrett's Esophagus, Presented at the 2012 ASCP Annual Meeting in Boston, MA Oct. 31-Nov. 3, 2012.

Zhu et al., Loss of Heterozygosities in Barrett Esophagus, Dysplasia and Adenocarcinoma, Annual Meeting Poster 1561, Presented at USCAP 2009, 2009.

*Primary Examiner* — Joseph Woitach
(74) *Attorney, Agent, or Firm* — Pepper Hamilton LLP

(57) ABSTRACT

Disclosed herein are methods for treating Barrett's metaplasia and esophageal adenocarcinoma and methods for determining mutational load as a predictor of the risk of disease progression from Barrett's metaplasia to esophageal adenocarcinoma.

9 Claims, 5 Drawing Sheets
(5 of 5 Drawing Sheet(s) Filed in Color)

METHODS FOR TREATING BARRETT'S METAPLASIA AND ESOPHAGEAL ADENOCARCINOMA

CROSS-REFERENCE TO RELATED APPLICATIONS

This application is a continuation-in-part of U.S. application Ser. No. 13/692,727 filed Dec. 3, 2012, which claims the benefit of U.S. Provisional Application Ser. No. 61/565,879 entitled "Methods for diagnosing low and high grade dysplasia in Barrett's esophagus" filed Dec. 1, 2011, U.S. Provisional Application Ser. No. 61/640,527 entitled "Methods for diagnosing low and high grade dysplasia in Barrett's esophagus" filed Apr. 30, 2012 and U.S. Provisional Application Ser. No. 61/661,256 entitled "Methods for diagnosing low and high grade dysplasia in Barrett's esophagus" filed Jun. 18, 2012, each of which are hereby incorporated herein by reference in their entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Not applicable

BRIEF SUMMARY OF THE INVENTION

Disclosed herein are methods for determining mutational load as a predictor of the risk of disease progression from Barrett's metaplasia to esophageal adenocarcinoma in a subject, the method comprising: amplifying DNA sequences from a biological specimen from the subject; detecting mutations in microsatellite regions of the amplified DNA sequences; categorizing clonality of each mutation; calculating a mutational load based on the sum of low and high clonality mutations; wherein calculating the mutational load further comprises assigning a score to each mutation based on detection of DNA microsatellite instability at a particular locus, calculating a mutational load based on the sum of low and high clonality mutations; wherein DNA microsatellite instability at a single locus is defined as $0.75z_1$, and wherein DNA microsatellite instability at multiple loci is defined as $0.75z_1+0.5z_2$, wherein $z_1$ represent a single locus displaying DNA microsatellite instability and $z_2$ is the number of loci displaying DNA microsatellite instability greater than 1 locus; wherein the score for low clonality is $0.5x$, wherein x is the number of low clonality mutations and the score for high clonality is y, wherein y is the number of high clonality mutations; and wherein the overall mutational load is $y+0.5x+0.75z_1+0.5z_2$; comparing the mutational load with a series of pre-determined mutational load cut-offs defining risk categories; and assigning the subject to a risk category corresponding to the subject's mutational load, wherein each risk category is indicative of the risk of disease progression.

In some embodiments, the pre-determined mutational load cut-offs defining risk categories are derived from a pre-determined patient population distribution with known mutational loads corresponding to a known disease state diagnosis.

In some embodiments, the known disease state diagnosis is selected from normal squamous, columnar epithelium without Barrett's metaplasia, Barrett's metaplasia, Barrett's metaplasia intermediate for dysplasia, low-grade dysplasia and high-grade dysplasia.

In some embodiments, the risk categories are selected from no mutational load, low mutational load, and high mutational load. In some embodiments, the subject is assigned to the no mutational load risk category when the subject has mutational load of 0.0. In some embodiments, no mutational load is indicative of no risk of disease progression from Barrett's metaplasia to esophageal adenocarcinoma. In some embodiments, no mutational load is indicative of the absence of actionable disease. In some embodiments, the absence of actionable disease is categorized as Barrett's metaplasia with a lower risk of progression than the baseline risk for Barrett's metaplasia, wherein surveillance of the patient can be safely discontinued.

In some embodiments, the subject is assigned to the low mutational load risk category when the subject has a mutational load greater than 0.0 but less 1.75. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the high mutational load risk category when the subject has a mutational load greater than or equal to 1.75. In some embodiments, a high mutational load is indicative of high risk of disease progression from Barrett's metaplasia to esophageal adenocarcinoma. In some embodiments, wherein a high mutational load is indicative of suitability of the subject for at least one treatment modality selected from endoscopic mucosal resection, radiofrequency ablation, cryoablation, endoscopic submucosal dissection, photodynamic therapy and combinations thereof.

In some embodiments, the subject is a human. In some embodiments, the subject is a human diagnosed with Barrett's esophagus.

In some embodiments, the biological specimen is a mucosal lining of the esophagus. In some embodiments, the biological specimen is representative of a disease region.

In some embodiments, amplifying DNA sequences comprises selecting a primer pair corresponding to a specific microsatellite region; adding the primer pair to the DNA sequences; and performing quantitative polymerase chain reaction on the DNA sequences with the primer.

In some embodiments, detecting mutations comprises determining the sequence of the amplified DNA and comparing the amplified DNA to a known wild type control sequence for the specific microsatellite region and identifying differences between the sequence of the amplified DNA and the known wild type control sequence.

In some embodiments, the specific microsatellite regions are selected from 1p (CMM1, Lmyc), 3p (VHL, OGG1), 5q (MCC, APC), 9p (CDKN2A, CDKN2B), 10q (PTEN, MXI1), 17p (TP53), 17q (NME1), 18q (DCC), 21q, 22q (NF2) and combinations thereof.

In some embodiments, categorizing clonality of each mutation comprises assigning one of three categories selected from the group consisting of no clonality, low clonality and high clonality.

In some embodiments, high clonality is assigned where loss of heterozygosity is present in greater than about 75% of DNA analyzed. In some embodiments, low clonality is assigned where loss of heterozygosity is present in about 50% to about 75% of DNA analyzed. In some embodiments, no clonality is assigned where loss of heterozygosity is present in less than about 50% of DNA analyzed.

In some embodiments, DNA microsatellite instability is determined by the presence of at least one of the shortening and lengthening of a DNA microsatellite region. In some embodiments, calculating a mutational load further comprises summing the clonality weighting for each specific microsatellite region showing a mutation or DNA microsatellite instability.

In some embodiments, determining mutational load as a predictor of disease progression is independent of a histological standard.

Disclosed herein are methods of treating a subject with a high risk of disease progression from Barrett's metaplasia to esophageal adenocarcinoma, the method comprising: amplifying DNA sequences from a biological specimen from the subject; detecting mutations in microsatellite regions of the amplified DNA sequences; categorizing clonality of each mutation; calculating a mutational load based on the sum of low and high clonality mutations; wherein calculating the mutational load further comprises assigning a score to each mutation based on detection of DNA microsatellite instability at a particular locus, calculating a mutational load based on the sum of low and high clonality mutations; wherein DNA microsatellite instability at a single locus is defined as $0.75z_1$, and wherein DNA microsatellite instability at multiple loci is defined as $0.75z_1+0.5z_2$, wherein $z_1$ represent a single locus displaying DNA microsatellite instability and $z_2$ is the number of loci displaying DNA microsatellite instability greater than 1 locus; wherein the score for low clonality is 0.5x, wherein x is the number of low clonality mutations and the score for high clonality is y, wherein y is the number of high clonality mutations; and wherein the overall mutational load is $y+0.5x+0.75z_1+0.5z_2$; comparing the mutational load with a series of pre-determined mutational load cut-offs defining risk categories; assigning the subject to a risk category corresponding to the subject's mutational load, wherein each risk category is indicative of the risk of disease progression; determining if the subject is in a risk category where treatment is indicated; and administering to the subject a at least one treatment modality selected from endoscopic mucosal resection, endoscopic submucosal dissection, a therapeutically effective amount of radiofrequency ablation, a therapeutically effective amount of cryoablation, a therapeutically effective amount of photodynamic therapy and combinations thereof.

In some embodiments, the pre-determined mutational load cut-offs defining risk categories are derived from a pre-determined patient population distribution with known mutational loads corresponding to a known disease state diagnosis. In some embodiments, the known disease state diagnosis is selected from normal squamous, columnar epithelium without Barrett's metaplasia, Barrett's metaplasia, Barrett's metaplasia intermediate for dysplasia, low-grade dysplasia and high-grade dysplasia.

In some embodiments, the risk categories are selected from no mutational load, low mutational load, and high mutational load. In some embodiments, the subject is assigned to the no mutational load risk category when the subject has mutational load of 0.0. In some embodiments, no mutational load is indicative of no risk of disease progression from Barrett's metaplasia to esophageal adenocarcinoma. In some embodiments, no mutational load is indicative of the absence of actionable disease. In some embodiments, the absence of actionable disease is categorized as Barrett's metaplasia with a lower risk of progression than the baseline risk for Barrett's metaplasia, wherein surveillance of the patient can be safely discontinued.

In some embodiments, the subject is assigned to the low mutational load risk category when the subject has a mutational load greater than 0.0 but less than 1.75. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the high mutational load risk category when the subject has a mutational load greater than 1.75. In some embodiments, a high mutational load is indicative of high risk of disease progression from Barrett's metaplasia to esophageal adenocarcinoma. In some embodiments, a high mutational load is indicative of suitability of the subject for at least one treatment modality selected from endoscopic mucosal resection, radiofrequency ablation, cryoablation, endoscopic submucosal dissection, photodynamic therapy and combinations thereof.

In some embodiments, the subject is a human. In some embodiments, the subject is a human diagnosed with Barrett's esophagus.

In some embodiments, the biological specimen is a mucosal lining of the esophagus. In some embodiments, the biological specimen is representative of a disease region.

In some embodiments, amplifying DNA sequences comprises selecting a primer pair corresponding to a specific microsatellite region; adding the primer pair to the DNA sequences; and performing quantitative polymerase chain reaction on the DNA sequences with the primer.

In some embodiments, detecting mutations comprises determining the sequence of the amplified DNA and comparing the amplified DNA to a known wild type control sequence for the specific microsatellite region and identifying differences between the sequence of the amplified DNA and the known wild type control sequence.

In some embodiments, the specific microsatellite regions are selected from 1p (CMM1, Lmyc), 3p (VHL, OGG1), 5q (MCC, APC), 9p (CDKN2A, CDKN2B), 10q (PTEN, MXI1), 17p (TP53), 17q (NME1), 18q (DCC), 21q, 22q (NF2) and combinations thereof.

In some embodiments, categorizing clonality of each mutation comprises assigning one of three categories selected from the group consisting of no clonality, low clonality and high clonality. In some embodiments, high clonality is assigned where loss of heterozygosity is present in greater than about 75% of DNA analyzed. In some embodiments, low clonality is assigned where loss of heterozygosity is present in about 50% to about 75% of DNA analyzed. In some embodiments, no clonality is assigned where loss of heterozygosity is present in less than about 50% of DNA analyzed.

In some embodiments, DNA microsatellite instability is determined by the presence of at least one of the shortening and lengthening of a DNA microsatellite region.

In some embodiments, calculating a mutational load further comprises summing the clonality weighting for each specific micro satellite region showing a mutation or DNA microsatellite instability.

In some embodiments, determining mutational load as a predictor of disease progression is independent of a histological standard.

DESCRIPTION OF DRAWINGS

The file of this patent contains at least one photograph or drawing executed in color. Copies of this patent with color drawing(s) or photograph(s) will be provided by the Patent and Trademark Office upon request and payment of the necessary fee.

DETAILED DESCRIPTION

Figure 1:
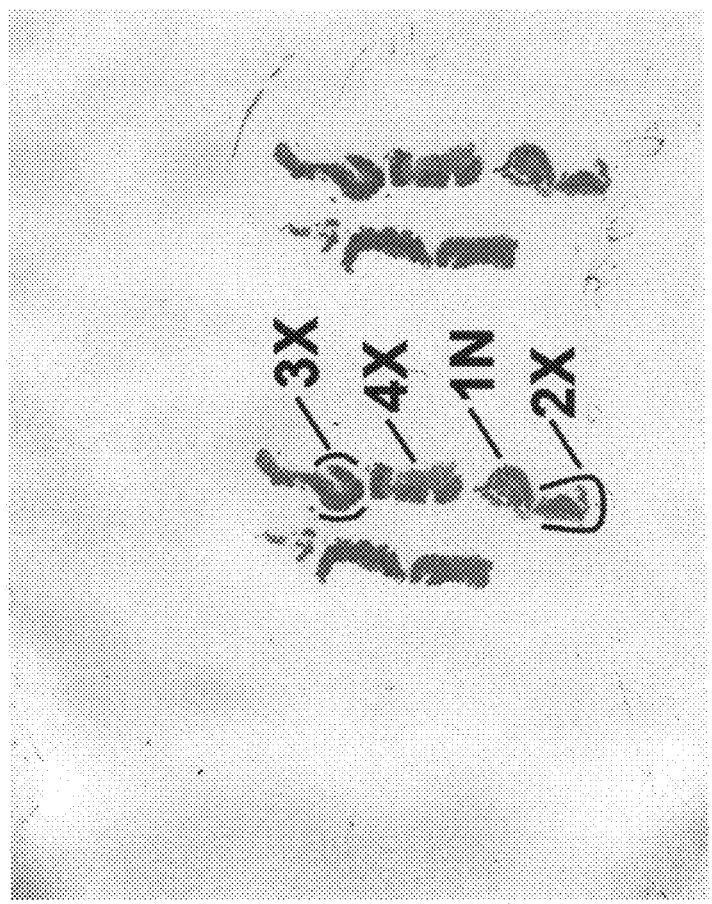
FIG. 1 depicts representative formalin-fixed, paraffin embedded (FFPE), hematoxylin and eosin (H&E) stained slide of Barrett's epithelium. Multiple re-cuts of several biopsies from the same patient are present on the slide. Multiple histological targets were microdissected from such slides for molecular analyses. 1N indicates a normal, non-Barrett's epithelial target used as a baseline control. 2x, 3x, and 4x indicate individual microdissected targets containing Barrett's epithelium.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must be noted that as used herein, the singular forms "a", "an", and "the" include plural referents unless the context clearly dictates otherwise. Thus, for example, reference to "a patient" includes a plurality of patients and so forth.

By "patient" and "subject" are meant to include any mammal including, but not limited to, humans, bovines, primates, equines, porcines, caprines, ovines, felines, canines, and any rodent (e.g., rats, mice, hamsters, and guinea pigs). In some embodiments, mammals include agricultural animals, domesticated animals, and primates, especially humans.

By "anomaly" is meant a broad, encompassing term to indicate a disease related change in a cell or tissue of an organ. Thus, "anomaly" includes cancer or dysplasia, a pre-cancerous neoplastic state, or a non-neoplastic condition. Pre-cancerous states include proliferative lesions that can span a spectrum from low-grade to high-grade neoplasia.

By "non-neoplastic condition" and "non-neoplastic abnormality" are meant to indicate specimens from sites known not to contain neoplasia. The non-neoplastic condition may be inflammatory or any adaptive state that may include features of cell proliferation but needs to be clearly discriminated from neoplasia.

"Biological specimen" is meant to include, but is not limited to, any sample containing DNA or cells from a subject. Such biological specimens include, but are not limited to, biopsies, fine needle aspirates, a cytology sample, a blood sample, a spinal tap, resected tissue, frozen tissue, blood sample, fixed tissue, a urine sample, a tissue swab (e.g., buccal swab or pap smear), and the like. In some embodiments, a biological specimen may include a fine needle aspiration; a biliary brushing; a core needle biopsy, an incisional biopsy, an excisional biopsy, or a combination thereof. In some embodiments, the biological specimen may be a breast lavage sample, an ascites fluid sample, fine needle aspirates from a cyst or other region of the subject's body, urine, blood, cerebrospinal fluid, a liquid cytology sample obtained by any medically available method, and/or saliva. The sample can contain cells or may contain only free-floating DNA (non-nuclear DNA) in the fluid sample. In some embodiments, the biological specimen is cellular, paucicellular, or cell-free which are meant to include the abundant presence of cells, the sparse presence of cells or the complete absence of cells respectively. The biological samples can be any sample containing DNA or cells from a patient. Such samples include but are not limited to fine needle aspirates, a cytology sample, a blood sample, a spinal tap, resected tissue, frozen tissue, blood sample, fixed tissue, a urine sample, a tissue swab (e.g., buccal swab or pap smear), and the like. In some embodiments, the biological specimen is a solid tissue section obtained from a subject. A biological specimen may include "tissue" and "cells" as well as "fluid samples". In further embodiments, the subject is a human with Barrett's metaplasia (BM). Biological specimens may be routinely fixed in standard fixative chemical agents, of any size including minute needle biopsy specimens and cell blocks of cytology material, and of any age including those stored in paraffin for over thirty years. Solid tissue specimens, removed at surgery or through biopsy procedures, may be exposed to fixative agents designed to prevent tissue breakdown and preserve morphologic integrity for microscopic analysis and archival storage.

"Tissue," and "cells," is meant to include resected tissue (fixed, stained, or treated), cytology specimens, blood and blood fractions from a patient or from a tissue bank. By "tumor aggressiveness" or "biological aggressiveness" are meant to include the phenotypic expression of a malignancy that is associated with increased adverse biological behavior. This includes phenomenon such as capacity for early metastatic seeding, capacity for wide visceral organ dissemination, rapid growth and invasion, lack of treatment responsiveness, short treated disease free interval and short overall patient survival.

By "clonal expansion" is meant a unidirectional process replacing precursor neoplastic cells with a dominant tumor cell population of cells with progressively more mutations.

By "tumor" is meant to include any malignant or non-malignant tissue or cellular containing material or cells. By "non-malignant tissue" is meant to include any abnormal tissue or cell phenotype and/or genotype associated with metaplasia, hyperplasia, a polyp, or pre-cancerous conditions (e.g., leukoplakia, colon polyps), regenerative change, physiologic adaption to stress or injury and cellular change in response to stress of injury. Tumor is meant to include solid tumors as well as leukemia's and lymphomas. "Neoplasm", "malignancy", and "cancer" are used interchangeably.

As used herein, "loss of heterozygosity" (LOH) is meant to include the loss of normal function of one allele of a gene in which the other allele was already inactivated. A common occurrence in cancer, loss of heterozygosity may indicate the absence of a functional tumor suppressor gene in a particular gene. In some embodiments, clonality or loss of heterozygosity is determined by detecting mutations in pre-determined regions of DNA. In some embodiments, the microsatellites are chosen to survey genomic instability by examining clonally expanded mutations in regions adjacent to, and in linkage disequilibrium with tumor suppressor genes commonly involved in many types of cancers. In some embodiments, the type of cancer is a carcinoma.

As used herein, "clonality" is meant to include but not limited to the state of a cell or cellular DNA. In some embodiments, clonality may represent the proportion of cells from a sample or sub-sample which is affected by a particular mutation or genetic alteration. In some embodiments, clonality may represent the proportion of cellular DNA from a sample or sub-sample which is affected by a particular mutation or genetic alteration. A tumor may derive from one mutated cell, wherein the progeny of this cell may be clones of the mutated cell and carry the same mutations such that they are technically a single clone of that cell. However, during course of cell division, it is possible for the progeny to acquire new mutations and acquire new characteristics to diverge as a new clone.

As used herein "microsatellite region" is meant to include, but is not limited to, repeating sequences of about 2-6 base pairs of DNA. The repeating sequence is often simple, consisting of two, three or four nucleotides (di-, tri-, and tetranucleotide repeats respectively), and can be repeated 3 to 100 times.

Barrett's metaplasia (BM), also known as Barrett's esophagus, predisposes to esophageal cancer, with the risk of progression closely associated with the presence and extent of dysplasia. Microscopic classification of dysplasia in can be subjective and, importantly, there are no histologic features that signal progression risk in early BM. BM is believed to be multifocal, and changes to the genome may precede morphological alteration and herald progression risk.

The management of BM is challenging due to 1) subjective microscopic classification with significant pathologist interpretation variability and 2) the need to better discriminate between stable, non-progressive intestinal metaplasia versus unstable disease progressing into dysplasia and to carcinoma. Early intervention is best applied to subjects with definitive pathology diagnosis and objective risk determination for progression.

Disclosed herein are methods for determining mutational load as a predictor of the risk of disease progression from BM to esophageal adenocarcinoma (EA) in a subject, the method comprising: amplifying DNA sequences from a biological specimen from the subject; detecting mutations in microsatellite regions of the amplified DNA sequences; categorizing clonality of each mutation; calculating a mutational load based on the sum of low and high clonality mutations; comparing the mutational load with a series of pre-determined mutational load cut-offs defining risk categories; and assigning the subject to a risk category corresponding to the subjects mutational load, wherein each risk category is indicative of the risk of disease progression.

In some embodiments, the pre-determined mutational load cut-offs defining risk categories are derived from a pre-determined patient population distribution with known mutational loads corresponding to a known disease state diagnosis.

In some embodiments, the known disease state diagnosis is selected from normal squamous, columnar epithelium without BM, BM, BM intermediate for dysplasia, low grade dysplasia (LGD) and high grade dysplasia (HGD).

In some embodiments, the risk categories are selected from no mutational load, low mutational load, and high mutational load. In some embodiments, the subject is assigned to the no mutational load risk category when the subject has mutational load of 0.0. In some embodiments, no mutational load is indicative of no risk of disease progression from BM to EA. In some embodiments, no mutational load is indicative of the absence of actionable disease. In some embodiments, actionable disease is categorized as.

In some embodiments, the subject is assigned to the low mutational load risk category when the subject has a mutational load greater than 0.0 but less than or equal to 2.0. In some embodiments, a low mutational load is indicative of a low risk of disease progression from BM to EA. In some embodiments, a low mutational load is indicative of suitability of the subject for monitoring.

In some embodiments, the subject is assigned to the high mutational load risk category when the subject has a mutational load greater than 2.0. In some embodiments, a high mutational load is indicative of high risk of disease progression from BM to EA. In some embodiments, a high mutational load is indicative of suitability of the subject for at least one treatment modality selected from endoscopic mucosal resection, radiofrequency ablation, cryoablation, endoscopic submucosal dissection, photodynamic therapy and combinations thereof.

In some embodiments, the subject is assigned to the low mutational load risk category when the subject has a mutational load greater than 0.0 but less than or equal to 1.0. In some embodiments, the subject is assigned to the high mutational load risk category when the subject has a mutational load greater than 1.0.

In some embodiments, the subject is assigned to the low mutational load risk category when the subject has a mutational load greater than 0.0 but less than or equal to 1.5. In some embodiments, the subject is assigned to the high mutational load risk category when the subject has a mutational load greater than 1.5.

In some embodiments, the subject is assigned to the low mutational load risk category when the subject has a mutational load greater than 0.0 but less than or equal to 2.5. In some embodiments, the subject is assigned to the high mutational load risk category when the subject has a mutational load greater than 2.5.

In some embodiments, the subject is assigned to the low mutational load risk category when the subject has a mutational load greater than 0.0 but less than or equal to 3.0. In some embodiments, the subject is assigned to the high mutational load risk category when the subject has a mutational load greater than 3.0.

In some embodiments, the subject is assigned to the low mutational load risk category when the subject has a mutational load greater than 0.0 but less than or equal to 3.5. In some embodiments, the subject is assigned to the high mutational load risk category when the subject has a mutational load greater than 3.5.

In some embodiments, the subject is assigned to the low mutational load risk category when the subject has a mutational load greater than 0.0 but less than or equal to 4.0. In some embodiments, the subject is assigned to the high mutational load risk category when the subject has a mutational load greater than 4.0.

In some embodiments, the subject is assigned to the low mutational load risk category when the subject has a mutational load greater than 0.0 but less than or equal to a mutational load of about 0.1 to about 5.0. In some embodiments, the subject is assigned to the high mutational load risk category when the subject has a mutational load greater than between 0.1 and 5.0.

In some embodiments, the risk categories are selected from no mutational load, low mutational load, and high mutational load. In some embodiments, the subject is assigned to the no mutational load risk category when the subject has mutational load of 0.0. In some embodiments, no mutational load is indicative of no risk of disease progression from Barrett's metaplasia to esophageal adenocarcinoma. In some embodiments, no mutational load is indicative of the absence of actionable disease. In some embodiments, the absence of actionable disease is categorized as Barrett's metaplasia with a lower risk of progression than the baseline risk for Barrett's metaplasia, wherein surveillance of the patient can be safely discontinued.

In some embodiments, the subject is assigned to the low mutational load risk category when the subject has a mutational load greater than 0.0 but less than 1.75. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the low mutational load risk category when the subject has a mutational load greater than 0.0 but less than 2.0. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the high mutational load risk category when the subject has a mutational load greater than 2.0. In some embodiments, the subject is assigned to the high mutational load risk category when the subject has a mutational load greater than or equal to 2.0. In some embodiments, the wherein a high mutational load is indicative of high risk of disease progression from Barrett's metaplasia to esophageal adenocarcinoma. In some embodiments, a high mutational load is indicative of suitability of the subject for at least one treatment modality selected from endoscopic mucosal resection, radiofrequency ablation, cryoablation, endoscopic submucosal dissection, photodynamic therapy and combinations thereof.

In some embodiments, the subject is assigned to the low mutational load risk category when the subject has a mutational load greater than 0.0 but less than or equal to 1.75. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the low mutational load risk category when the subject has a mutational load greater than 0.0 but less than 1.75. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the high mutational load risk category when the subject has a mutational load greater than 1.75. In some embodiments, the subject is assigned to the high mutational load risk category when the subject has a mutational load greater than or equal to 1.75. In some embodiments, the wherein a high mutational load is indicative of high risk of disease progression from Barrett's metaplasia to esophageal adenocarcinoma. In some embodiments, a high mutational load is indicative of suitability of the subject for at least one treatment modality selected from endoscopic mucosal resection, radiofrequency ablation, cryoablation, endoscopic submucosal dissection, photodynamic therapy and combinations thereof.

In some embodiments, the pre-determined mutational load cut-offs are variable. In some embodiments, the subject is assigned to the low mutational load risk category when the subject has a mutational load greater than 0.0 but less than or equal to a mutation load ranging from about 1.75 to about 2.0. In some embodiments, the subject is assigned to the low mutational load risk category when the subject has a mutational load greater than 0.0 but less than a mutation load ranging from about 1.75 to about 2.0. In some embodiments, the subject is assigned to the high mutational load risk category when the subject has a mutational load greater from about 1.75 to about 2.0. In some embodiments, the subject is assigned to the high mutational load risk category when the subject has a mutational load greater than or equal from about 1.75 to about 2.0.

In some embodiments, the subject is a human. In some embodiments, the subject is a human diagnosed with BM. In some embodiments, the biological specimen is a mucosal lining of the esophagus. In some embodiments, the biological specimen comprises the mucosal lining of the esophagus. In some embodiments, the biological specimen comprises a deeper tissue type. These deeper tissue types are capable of forming sarcomas. In other embodiments, the specimen is a tissue section. In some embodiments, the biological specimen is representative of a disease region.

In some embodiments, the biological specimen is a formalin-fixed, paraffin embedded tissue section. In some embodiments, the tissue section is from the esophagus of the subject. In yet other embodiments, the biological specimen is a fresh section of esophagus. In some embodiments, biological specimens are selected for the presence of BM. In other embodiments, selection is accomplished by identification of histological features characteristic of BM. In some embodiments, biological specimens are selected independently of a histological standard.

In some embodiments, the subject is a human with squamous dysplasia. The majority of EA cases arise from BM were the squamous mucosa transforms first to a mucinous lining and then to a mucinous cancer. This is defined for about 80% of EA cases. The remainder is squamous cancers where the squamous lining directly transforms to squamous cancer. In some embodiments, the subject is a human diagnosed with esophageal squamous cancer.

In some embodiments, amplifying DNA sequences comprises selecting a primer pair corresponding to a specific microsatellite region; adding the primer pair to the DNA sequences; and performing quantitative polymerase chain reaction on the DNA sequences with the primer.

In some embodiments, the first step in the qPCR process is to adjust the DNA concentration to a value of about 5 ng/µL so that the absolute amount of DNA present in each reaction is the same, but so that the integrity may vary which is the purpose of the analysis. 5 ng/µL is preferred as it has been found to be a minimal value for robust amplification. In some embodiments, other amounts may be used. For example, from about 10 ng/µL to about 10 µg/µL and more preferably from about 5 ng/µL to about 5 µg/µL may be used.

In some embodiments, the number of qPCR cycles may be used as a marker of DNA quality. The lower the number cycles required to reach a desired threshold is indicative of higher quality DNA. In general, if over 30 cycles are required, then the DNA quality is considered suboptimal due to, for example, allelic imbalance resulting from inadequate amounts of template DNA. Specifically, Ct values (i.e., threshold values for quantitative PCR product detection) over 30.0 cycles is considered evidence of poor quality of DNA, especially if the DNA quantity present is above 2.0 ng/µL. Ct values of 29.0-30.0 are considered borderline. Values of 29.0 or less are indicative of good quality DNA.

In some embodiments, DNA quality may be further assessed by performing competitive template polymerase chain reaction (PCR) amplification for a unique pair of genes, (e.g., Glucocerebrosidase Gene and its pseudogene) at a particular point where the two genes have virtually identical sequences, with the exception of a 55 base pair deletion in the pseudogene. This is not the only gene that can serve this purpose. In some embodiments, any pairing of gene or genomic segments of similar sequence but differences in length can be substituted.

In some embodiments, this PCR reaction creates two amplicons that are identical in sequence except for the deletional region. During the reaction, a competition exists between the two similar templates (but having different lengths). In some embodiments, the degree of DNA degradation in the sample will be reflected by less effective amplification of the longer template as compared to the shorter template. In some embodiments, this serves as a measure of DNA integrity. In some embodiments, the amount of each product, short and long, may be quantitatively measured by capillary electrophoresis. Methods of performing the PCR reaction and electrophoresis are well known in the art. In some embodiments, reagents are added to the final sample the purpose of which is to enhance DNA availability, to enhance the ability to amplify the DNA, and DNA quantity. In some embodiments, any system that utilizes similar primers to amplify products of different lengths can be substituted.

The procedure for qPCR and PCR amplification has been well described and variations on its performance will not impact the various embodiments of the invention. In some embodiments, the recommended procedures of the manufacturers for the PCR reagents are closely followed (GeneAmp kit, Applied Biosystems). In some embodiments, other commercial and non-commercial systems for qPCR and PCR amplification can be readily substituted. In some embodiments, the qPCR or PCR reaction is performed in a manner that is highly robust, especially when using minute DNA samples. By "robust" in this context is meant a qPCR or PCR reaction that reliably generates abundant amplified DNA that accurately reflects the starting composition mixture of normal and mutated DNA derived from a particular specimen. Reagents such as dimethylsulfoxide or dextran sulfate may be added to the amplification reaction to enhance amplification. In some embodiments, other similar reagents can be substituted. In some embodiments, manipulations, such as nested PCR, may be performed to further enhance amplification.

In some embodiments, DNA is amplified from fixative treated biological specimens. Once DNA amplification has been carried out from a fixative treated biological specimen it is vital that rigorous separation of primers and most importantly small sized nonspecific amplification products may be performed in such a way as to isolate the desired amplification product as purely as possible. Due to the factors listed above, fixative treated biological specimens tend to produce a relatively greater amount of such nonspecific products, which can be seen as a smear effect on horizontal gel electrophoresis. If these products are carried into the subsequent genotyping steps such as DNA sequencing, they may result in artificial bands or weak ineffective sequencing reactions. One approach to isolating specific amplification product is to carry out agarose gel electrophoresis at relatively high agarose concentrations such as 3% to free the desired appropriate amplification product from nonspecific contaminants.

A rate limiting step when handling fixative treated biological specimens for genetic analysis may be effective and specific DNA amplification. Unlike pure DNA that is extracted from fresh or frozen tissues, DNA that has been exposed to chemical fixative such as formaldehyde are often unsuccessfully or only poorly amplified. While the reason for the inability to efficiently amplify fixed tissues is known to be related to chemical action of the fixative agent upon nucleic acids, the precise mechanism most directly related to poor amplification is only poorly understood. The most suitable measures to overcome this detrimental effect are therefore not fully appreciated. Instead, recourse is usually taken to sacrificing large amounts of fixative treated tissue or abandoning the use of fixative treated tissues altogether.

In some embodiments, any region of a gene can be amplified provided sufficient sequence information is available upon which to formulate amplifying and sequencing primers; short DNA sequences, such as 18-30 base pair long, most easily created by means of an oligonucleotide synthesizer apparatus. In some embodiments, these primers direct the amplification and sequencing of DNA. Oligonucleotide primer pairs are usually designed to amplify a genomic region approximately 200 base pairs in length, although longer lengths can be effectively amplified from fixative treated tissues. Either amplifying primer can serve as a sequencing primer, but design and use of an internal primer may in some case be worthwhile to achieve a clean sequencing band pattern. As sequencing will be performed by means of dideoxy chain termination with $^{35}$S radionucleotide incorporation, it is important to select a radionucleotide that will be incorporated as close to the 30 end of the ultimate sequencing primer, ideally within three bases and several times within the first 10 bases.

In some embodiments, DNA sequences from a biological specimen or amplified DNA can be analyzed for quantity, quality or a combination thereof. In some embodiments, optical density (OD) analysis is performed to quantify the DNA. One approach uses the nanodrop technique, because it requires only one microliter to be sacrificed for the purpose of obtaining the DNA concentration. Other techniques for quantifying DNA will serve quite adequately for this purpose. In some embodiments, the higher optical density (OD) value the larger amount of DNA is present. In some embodiments, the quantity of DNA extracted can vary.

In some embodiments, the DNA can be quantified by measurement of the optical density to fluorescent light at wavelengths of 230, 260, and 280 nm. The 260/280 and 260/230 ratios may be 1.7-2.0, in keeping with extraction of purified DNA and for the purpose to exclude protein and other contaminants. In some embodiments, any technique that defines the amount of DNA in the sample can be a suitable substitute.

In some embodiments, DNA quality, or degree of degradation is also determined. To measure DNA quality, quantitative PCR (qPCR) may be performed followed by competitive template PCR as described above. Using the concept that a longer sized PCR product would be present in relatively lesser amounts than a shorter sized product due to greater chance for strand breakage as a result of DNA degradation, a competitive duplex PCR reaction of highly similar DNA sequence but differing in length is needed. In some embodiments, this can be accomplished by simply carrying out a short and long product PCR reaction in one container (e.g., test tube) on one source of DNA.

In some embodiments, to measure DNA quality, quantitative PCR (qPCR) is performed and is followed by competitive template PCR. The qPCR reaction can be performed using sybr green as the indicator in a suitable thermo cycler capable of measuring fluorescence during the amplification process as this is the simplest and least costly technique. Other techniques for qPCR determination using fluorescent labeled primers can substitute just as well. Known quantitative controls and replicate analysis of samples may be used to standardize amplification reactions and is recommended; the exact use and configuration of controls and replicate analysis may be varied as determined by the user. Standardization of quantitative PCR amplification of the first exon of the K-ras-2 gene may be used. In some embodiments, any PCR product from any gene or genomic segment that amplifies reliably may be effectively used.

In some embodiments, detecting mutations comprises determining the sequence of the amplified DNA and comparing the amplified DNA to a known wild type control sequence for the specific microsatellite region and identifying differences between the sequence of the amplified DNA and the known wild type control sequence.

In some embodiments, detecting mutations comprises determining the sequence of the amplified DNA by capillary gel electrophoresis and comparing the amplified DNA to a known wild type control sequence for the specific microsatellite regions. Wild type sequences can be obtained from databases known to those skilled in the art. In some embodiments, the NCBI database may be used to design primers and obtain current sequence information. In some embodiments, the Ensembl database may be used to cross reference a sequence and determine the intron-exon boundaries for a particular gene. In some embodiments, sequences may be obtained from the UCSC Genome Bowser, the NCBI databases or combinations thereof.

In some embodiments, the specific microsatellite regions are selected from 1p (CMM1, Lmyc), 3p (VHL, OGG1), 5q (MCC, APC), 9p (CDKN2A, CDKN2B), 10q (PTEN, MXI1), 17p (TP53), 17q (NME1), 18q (DCC), 21q, 22q (NF2) and combinations thereof.

In some embodiments, mutations are in detected in specific chromosomal regions. In certain embodiments, the regions including but not limited to those in the table below or combinations thereof. In some embodiments, the microsatellite panel is comprised of the chromosomal regions in the table 1 below.

In some embodiments, primers flanking a specific chromosomal region can be designed based on currently known primer design principles of DNA sequencing. In some embodiments, primer sets flanking one or more of the chromosomal regions described in the table below can be designed based on currently known primer design principles of DNA sequencing.

In some embodiments, primers flanking a specific chromosomal region can be designed based on currently known primer design principles of PCR. In some embodiments, primer sets flanking one or more of the chromosomal regions described in the table below can be designed based on currently known primer design principles of PCR.

Table 1—Chromosomal Markers and Specific Loci

TABLE 1

| Chromosomal Markers and specific loci | | | |
|---|---|---|---|
| Name | UCSC STS ID | UniSTS_NUM | Locus |
| Gaucher E9 | | | 1q22 |
| LMYC 5NT | | | 1p34.2 |
| D1s1172 | 98555 | 3115 | 1p22.3 |
| D1s1139 | 5461 | 149324 | 1p36.21 |
| D1s407 | 5418 | 72197 | 1p36.21 |
| B Catenin E3 | | | B Catenin E3 |
| RARB INS/DEL1 | | | 3p25 |
| D3s1542 | 5794 | 55484 | 3p12.3 |
| D3s1745 | 10445 | 51439 | 3p22.3 |
| D3s2303 | 163052 | 149055 | 3p24.3 |
| D3s1539 | 5789 | 40803 | 3p26.3 |
| D3s2318 | 5822 | 149264 | 3p11.2 |
| D3s2327 | 5836 | 149354 | 3p24.2 |
| CKIT E11 | | | C-KIT E11 |
| CKIT E13 | | | |
| CKIT E17 | | | C-KIT E17 |
| PDGFRA E12 | | | |
| PDGFRA E18 | | | |
| CKIT E9 | | | |
| D5s592 | 106793 | 31251 | 5q23.1 |
| D5s615 | 6148 | 3012 | 5q23.2 |
| BRAF E15 | | | BRAF E15 |
| EGFR E 19 | | | EGFR E 19 |
| EGFR E 21 | | | EGFR E 21 |
| D7s1818 | 6380 | 31908 | 7p12.3 |
| D7s1831 | 13624 | 45284 | 7p12.1 |
| D9s251 | 6713 | 33733 | 9p21.1 |
| D9s254 | 6718 | 67103 | 9p23 |
| D10s1173 | 6888 | 149379 | 10q23.32 |
| D10s520 | 6894 | 47225 | 10q23.33 |

TABLE 1-continued

Chromosomal Markers and specific loci

| Name | UCSC STS ID | UniSTS_NUM | Locus |
|---|---|---|---|
| HRAS1 E1 | | | HRAS1 E1 |
| KRAS2 E1 | | | Kras2.E1 |
| KRAS2 E2 | | | Kras2.E2 |
| D17s1161 | 7596 | 149246 | 17q22 |
| D17s1299 | 7524 | 62207 | 17q21.2 |
| D17s2183 | 98494 | 2914 | 17q11.2 |
| D17s974 | 7532 | 11768 | 17p13.1 |
| D17s1289 | 120250 | 74161 | 17p13 |
| P53 I1 | | | 17p13.1 |
| D18s814 | 109741 | 40087 | 18q21.33 |
| D19s400 | 7781 | 34989 | 19q13.2 |
| D19s559 | 7794 | 149330 | 19q13.32 |
| D21s1244 | 7925 | 57172 | 21q21.2 |
| D22s532 | 7958 | 16487 | 22q13.2 |
| AMELOGENIN | | | Xp22.2 |

PCR amplification may be used to generate amplicons of less than 200 nucleotides using synthetic oligonucleotide primers flanking each microsatellite. Allele peak heights and lengths may be used to define the presence or absence of allelic imbalance and clonality (i.e., LOH) for a given sample. Allelic imbalance is reported when the ratio of polymorphic allelic bands for a particular marker is beyond about 95% confidence limits for the variation in peak heights for individual allele pairings derived from analysis using non-neoplastic specimen samples. In general, this is below about 0.5 or above about 2.0. Preferably, the allele ratio is two standard deviations beyond the average for the ratio of the specific pairing of polymorphic alleles. This will provide a low threshold for detection of significant allelic imbalance (LOH), however other algorithms for defining LOH can be used, so long as they are applied uniformly across different specimens. It is understood that minor degrees of LOH will not be detected. However, this is not a drawback, because these minor LOH mutations may not be causally related to clonal expansion or provides significant malignant growth properties.

In some embodiments, allelic imbalance mutations are treated as genomic deletions associated with tumor suppressor genes. The ratio of allele peak heights is a measure of an admixture of mutated and non-mutated cells or DNA, and varies according to the individual pairing of specific microsatellite marker alleles. Allele ratios of 2.0 or 0.5 is said to be present when 50% of the total DNA is derived from cells possessing the loss. The deviation from ideal normal ratio of 1.0 indicates which specific allele was affected. Allele ratios below about 0.5 or above about 2.0 are mathematically correlated with the proportion of cells affected by genomic loss.

In some embodiments, allelic imbalance determination can be carried out as follows. Post-amplification products are electrophoresed and relative fluorescence determined for individual allele peak height. The ratio of peaks is calculated by dividing the value for the shorter-sized allele by that of the longer-sized allele. Thresholds for significant allelic imbalance have been determined beforehand in studies using normal (i.e., non-neoplastic) specimens representing each unique pairing of individual alleles for every marker used in the panel. In Some embodiments, the normal range of variability is established for a particular marker. In further embodiments, the range may be characterized by two standard deviations, or quantiles of the distribution of peak height ratios, or similar techniques aimed at characterizing normal variation of the marker in non-mutated DNA. Peak height ratios falling outside of the normal range of variability are assessed as showing significant allelic imbalance. In each case, the non-neoplastic tissue targets are used to establish informativeness status and then to determine the individual pattern of polymorphic marker alleles. Having established significant allelic imbalance, it is then possible to calculate the proportion of cellular DNA that was subject to hemizygous loss. For example, a polymorphic marker pairing whose peak height ratio was ideally 1.00 in normal tissue with a standard deviation in non-neoplastic tissue of 0.23, could be inferred to have 50% of its cellular content affected by hemizygous loss if the peak height ratio was 0.5 or 2.0. This requires that a minimum of 50% of the DNA in a given sample be derived from cells possessing deletion of the specific microsatellite marker. The deviation from ideal normal ratio of 1.0 indicated which specific allele was affected. In a similar fashion, allele ratios below 0.5 or above 2.0 could be mathematically correlated with the proportion of cells affected by genomic loss. Other algorithms for quantitative determination of allelic imbalance can be used with equal effectiveness.

In some embodiments, categorizing clonality of each mutation comprises assigning one of three categories selected from the group consisting of no clonality, low clonality and high clonality. In some embodiments, high clonality is assigned where loss of heterozygosity is present in greater than about 75% of DNA analyzed. In some embodiments, low clonality is assigned where loss of heterozygosity is present in about 50% to about 75% of DNA analyzed. In some embodiments, no clonality is assigned where loss of heterozygosity is present in less than about 50% of DNA analyzed.

In some embodiments microsatellite mutation detection, and allelic imbalance indicates copy number change. In some embodiments, clonality is interpreted as the percentage of cells affected by a copy number change, nominally a deletion that confers loss of heterozygosity in a linked tumor suppressor gene. In some embodiments, clonality is interpreted as the percentage of DNA affected by a copy number change, nominally a deletion that confers loss of heterozygosity in a linked tumor suppressor gene.

In some embodiments, allelic imbalance mutations are treated as genomic deletions associated with tumor suppressor genes. The ratio of allele peak heights is a measure of an admixture of mutated and non-mutated cells or DNA, and varies according to the individual pairing of specific microsatellite marker alleles. Allele ratios of 2.0 or 0.5 is said to be present when 50% of the total DNA is derived from cells possessing the loss. The deviation from ideal normal ratio of 1.0 indicates which specific allele was affected. Allele ratios below about 0.5 or above about 2.0 are mathematically correlated with the proportion of cells affected by genomic loss.

In some embodiments, determining clonality can be carried out as follows. Post-amplification products are electrophoresed and relative fluorescence determined for individual allele peak height. The ratio of peaks is calculated by dividing the value for the shorter-sized allele by that of the longer-sized allele. Thresholds for significant allelic imbalance have been determined beforehand in extensive studies using normal (i.e., non-neoplastic) specimens representing each unique pairing of individual alleles for every marker being used. Peak height ratios falling outside of two standard deviations beyond the mean for each polymorphic allele pairing were assessed as showing significant allelic imbalance. In each case, the non-neoplastic tissue targets are used to establish informativeness status and then to determine the individual pattern of polymorphic marker alleles. Having established significant allelic imbalance, it is then possible to calculate the proportion of cellular DNA that was subject to hemizygous loss. For example, a polymorphic marker pairing whose peak height ratio was ideally 1.00 in normal tissue with a standard deviation in non-neoplastic tissue of 0.23, could be inferred to have 50% of its cellular content affected by hemizygous loss if the peak height ratio was 0.5 or 2.0. This requires that a minimum of 50% of the DNA in a given sample be derived from cells possessing deletion of the specific microsatellite marker. The deviation from ideal normal ratio of 1.0 indicated which specific allele was affected. In a similar fashion, allele ratios below 0.5 or above 2.0 could be mathematically correlated with the proportion of cells affected by genomic loss. Other algorithms for quantitative determination of allelic imbalance can be used with equal effectiveness.

In some embodiments, calculating the mutational load comprises assigning a score to each mutation based on a categorization of low or high clonality of each mutation, wherein the score for low clonality is 0.5x, wherein x is the number of low clonality mutations and the score for high clonality is y, wherein y is the number of high clonality mutations; and wherein the overall mutational load is y+0.5x. In some embodiments, mutation load can be expressed generally as $ML=x*W_{Low}+y*W_{High}$, where $W_{Low}$ and $W_{High}$, are weightings for low and high clonality respectively.

In some embodiments, calculating the mutational load further comprises assigning a score to each mutation based on detection of DNA microsatellite instability at a particular locus, wherein DNA microsatellite instability at a single locus is defined as 0.75z, wherein z is the number of loci displaying DNA microsatellite instability; wherein the score for low clonality is 0.5x, wherein x is the number of low clonality mutations and the score for high clonality is y, wherein y is the number of high clonality mutations; and wherein the overall mutational load is y+0.5x+0.75z. In some embodiments, DNA microsatellite instability is determined by the presence of at least one of the shortening and lengthening of a DNA microsatellite region. In some embodiments, the emergence of new alleles, manifested as DNA microsatellite instability mutations" as this is the first MSI that has been seen in these markers.

In some embodiments, calculating the mutational load further comprises assigning a score to each mutation based on detection of DNA microsatellite instability at multiple loci, wherein DNA microsatellite instability at multiple loci is defined as 2z, wherein z is the number of loci displaying DNA microsatellite instability; wherein the score for low clonality is 0.5x, wherein x is the number of low clonality mutations and the score for high clonality is y, wherein y is the number of high clonality mutations; and wherein the overall mutational load is y+0.5x+2z. In some embodiments, DNA microsatellite instability is determined by the presence of at least one of the shortening and lengthening of a DNA microsatellite region. In some embodiments, the emergence of new alleles, manifested as DNA microsatellite instability mutations" as this is the first MSI that has been seen in these markers.

In some embodiments, calculating the mutational load further comprises assigning a score to each mutation based on detection of DNA microsatellite instability at multiple loci, wherein DNA microsatellite instability at multiple loci is defined as 1z, wherein z is the number of loci displaying DNA microsatellite instability; wherein the score for low clonality is 0.5x, wherein x is the number of low clonality mutations and the score for high clonality is y, wherein y is the number of high clonality mutations; and wherein the overall mutational load is y+0.5x+1z. In some embodiments, DNA microsatellite instability is determined by the presence of at least one of the shortening and lengthening of a DNA microsatellite region. In some embodiments, the emergence of new alleles, manifested as DNA microsatellite instability mutations" as this is the first MSI that has been seen in these markers.

In some embodiments, calculating the mutational load further comprises assigning a score to each mutation based on detection of DNA microsatellite instability at multiple loci, wherein DNA microsatellite instability at multiple loci is defined as 0.5z, wherein z is the number of loci displaying DNA micro satellite instability; wherein the score for low clonality is 0.5x, wherein x is the number of low clonality mutations and the score for high clonality is y, wherein y is the number of high clonality mutations; and wherein the overall mutational load is y+0.5x+0.5z. In some embodiments, DNA microsatellite instability is determined by the presence of at least one of the shortening and lengthening of a DNA microsatellite region. In some embodiments, the emergence of new alleles, manifested as DNA microsatellite instability mutations" as this is the first MSI that has been seen in these markers.

In some embodiments, calculating the mutational load further comprises assigning a score to each mutation based on detection of DNA microsatellite instability at a particular locus, wherein DNA microsatellite instability at a single locus is defined as $0.75z_1$, and wherein DNA microsatellite instability at multiple loci is defined as $0.5z_2$, wherein $z_1$ is the number of loci displaying DNA microsatellite instability and $z_2$ is the number of loci displaying DNA microsatellite instability greater than 1; wherein the score for low clonality is 0.5x, wherein x is the number of low clonality mutations and the score for high clonality is y, wherein y is the number of high clonality mutations; and wherein the overall mutational load is $y+0.5x+0.75z_1+0.5z_2$.

In some embodiments, calculating the mutational load further comprises assigning a score to each mutation based on detection of DNA microsatellite instability at a particular locus, wherein DNA microsatellite instability at a single locus is defined as $0.75z_1$, and wherein DNA microsatellite instability at multiple loci is defined as $0.75z_1+0.5z_2$, wherein $z_1$ represent a single locus displaying DNA microsatellite instability and $z_2$ is the number of loci displaying DNA microsatellite instability greater than 1 locus; wherein the score for low clonality is 0.5x, wherein x is the number of low clonality mutations and the score for high clonality is y, wherein y is the number of high clonality mutations; and wherein the overall mutational load is $y+0.5x+0.75z_1+0.5(z_2)$. In some embodiments $z_1=1$. By way of example, were 3 MSI mutations are detected, the above equation can be expressed as follows: mutational load=y+0.5x+0.75(1)+0.5 (2). Where a single MSI mutation is detected, the equation is expressed as follows: mutational load=y+0.5x+0.75(1).

In some embodiments, calculating a mutational load further comprises summing the clonality weighting for each specific micro satellite region showing a mutation or DNA microsatellite instability.

In some embodiments, weightings for high clonality mutations range from 2.0 to 2.5, and those for low clonality mutations range from 1 to 1.4. Since the absolute overall score can be arbitrarily scaled (i.e. 1-10 or 1-100 can be equivalent scores), any weighting maintaining these proportions will produce equivalent cutoffs scaled by the chosen scaling factor.

In some embodiments, the overall score for a case is the maximum score of any target. This is consistent with standard practice in microscopic evaluation of Barrett's esophagus and many other neoplastic conditions.

In some embodiments, particular weightings may be assigned to a particular mutation, DNA microsatellite region or a combination thereof. In some embodiments, weightings are equal for all mutations in particular DNA microsatellite regions analyzed. In some embodiments, mutations in particular DNA microsatellite regions may be given higher weightings than other mutations in particular DNA microsatellite regions. In some embodiments, certain mutations in particular DNA microsatellite regions may have a greater influence on the ML for a particular subject. In some embodiments, mutations in particular DNA microsatellite regions may include, but are not limited to mutations in 17p (TP53) and 9p (CDKN2A, CDKN2B).

In some embodiments, calculating a mutational load further comprises assigning a distinct weighting for a mutation depending on the genomic locus of the mutations. Thus a low clonality mutation at 17p (TP53) or 9p (p16) may be weighted as 0.55 up to 0.75 rather than 0.5, and a high clonality mutation may be weighted as 1.05 up to 1.5.

In some embodiments, multiple microsatellite markers may flank a particular tumor suppressor gene. In these embodiments, the count of mutations may count the presence of any or all mutations for a given locus (i.e. all markers in proximity to a particular tumor suppressor, or if only one tumor suppressor gene per chromosome arm is interrogated, all markers per chromosome arm) as a single mutation.

In some embodiments, weighting of mutation is defined and clonality is determined by statistical techniques such as logistic regression, discriminant analysis or machine learning techniques such as neural networks or support vector machines. Many such techniques will also produce estimated cut-offs between distinct disease states in the progression of BM (i.e., between disease states of non-dysplastic BM (i.e., intestinalized columnar mucosal metaplasia).

In some embodiments, cut-offs may be calculated without regression by use of receiver-operator characteristics to define desired performance characteristics of a particular cut-off depending the desired balance of test performance characteristics (e.g. sensitivity, specificity and overall accuracy).

In some embodiments, analysis of clonal diversity can supplement the embodiments described herein. In some embodiments, clonal diversity can in addition to the embodiments described herein serve as a factor in the prediction of disease progression.

In some embodiments, the presence of a mutation spanning multiple markers near a particular tumor suppressor gene can serve as additional weighting for a mutation. In some embodiments, this weighting is 0.25 per additional microsatellite marker affected (i.e., 1.25 for a high clonality mutation where 2 markers are affected, 1.5 where 3 are affected, etc.). In some embodiments, mutations with lengths of mutated segment of DNA greater than 5 million base pairs, measured by the number of base pairs between distinct microsatellite markers at the same genomic locus are given an extra weighting above that assigned for clonality. In some embodiments, mutations affecting more than 1 million bases are given an extra weighting of 0.25. In some embodiments, mutations affecting more than 5 million base pairs are given an extra weighting of 0.5

In some embodiments, determining mutational load is independent of a histological standard. In some embodiments, microscopic slides associated with a biological specimen, if present, are first reviewed, as well as any clinical information pertinent to the individual patient. In some embodiments, analysis of DNA from a biological specimen can be performed without preliminary review of microscopic features.

Some embodiments are directed to methods of identifying the presence of dysplasia in a subject comprising: amplifying DNA sequences from a biological specimen from a subject with Barrett's esophagus; detecting mutations in specific microsatellite regions of amplified DNA sequences; categorizing clonality to each mutation; calculating a clonality weighting for each mutation; calculating a weighted mutation count; and comparing the weighted mutation count with a cut-off weighted mutation count, wherein a weighted mutation count above the cut-off weighted mutation count indicates the presence of dysplasia.

In some embodiments, the weighted mutation count may indicate a greater degree of neoplastic change than is evident from morphologic change on histology examination. For example, regions of intestinal metaplasia taken from a patient with dysplasia can show a greater degree of change than intestinal metaplasia from a non-dysplastic patient. This "progressor metaplasia" may indicate more advanced disease in the patient than is indicated by morphologic inspection. This may explain why a substantial proportion of esophageal adenocarcinoma patients present without a previous diagnosis of dysplasia. The detection of progressor metaplasia may be used to determine risk of disease progression in a non-dysplastic patient, which in turn may be used to determine the appropriateness of therapeutic interventions such as radiofrequency ablation of the esophagus.

In some embodiments, techniques to relate independent variables to class-based outcomes/dependent variables can used to predict non-dysplastic or dysplastic disease from number and clonality of mutations, including linear discriminant analysis to discriminate non-dysplastic from dysplastic disease, and including regression technique such as proportional odds logistic regression to predict disease state based on number and clonality of mutations.

In some embodiments, the cut-off weighted mutation count cut-off separating low grade dysplasia from high grade dysplasia is 5.3. In some embodiments, the cut-off weighted mutation count cutoff separating low grade dysplasia from high grade dysplasia is 7.9.

Some embodiments are directed to methods of treating a subject with a high risk of disease progression from Barrett's metaplasia to esophageal adenocarcinoma, the method comprising: amplifying DNA sequences from a biological specimen from the subject; detecting mutations in microsatellite regions of the amplified DNA sequences; categorizing clonality of each mutation; calculating a mutational load based on the sum of low and high clonality mutations; comparing the mutational load with a series of pre-determined mutational load cut-offs defining risk categories; assigning the subject to a risk category corresponding to the subjects mutational load, wherein each risk category is indicative of the risk of disease progression; determining if the subject is in a risk category where treatment is indicated; and administering to the subject a at least one treatment modality selected from endoscopic mucosal resection, endoscopic submucosal dissection, a therapeutically effective amount of radiofrequency ablation, a therapeutically effective amount of cryoablation, a therapeutically effective amount of photodynamic therapy and combinations thereof.

In some embodiments, the pre-determined mutational load cut-offs defining risk categories are derived from a pre-determined patient population distribution with known mutational loads corresponding to a known disease state diagnosis.

In some embodiments, the known disease state diagnosis is selected from normal squamous, columnar epithelium without Barrett's metaplasia, Barrett's metaplasia, Barrett's metaplasia intermediate for dysplasia, low grade dysplasia and high grade dysplasia.

In some embodiments, the risk categories are selected from no mutational load, low mutational load, and high mutational load.

In some embodiments, the subject is assigned to the no mutational load risk category when the subject has mutational load of 0.0. In some embodiments, no mutational load is indicative of no risk of disease progression from Barrett's metaplasia to esophageal adenocarcinoma. In some embodiments, no mutational load is indicative of the absence of actionable disease. In some embodiments, no actionable disease is categorized as Barrett's metaplasia with a lower risk of progression than the baseline risk for Barrett's metaplasia, such that surveillance of the patient can be safely discontinued.

In some embodiments, the subject is assigned to the low mutational load risk category when the subject has a mutational load greater than 0.0 but less than or equal to 2.0. In some embodiments, the wherein a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the high mutational load risk category when the subject has a mutational load greater than 2.0. In some embodiments, a high mutational load is indicative of high risk of disease progression from Barrett's metaplasia to esophageal adenocarcinoma. In some embodiments, a high mutational load is indicative of suitability of the subject for at least one treatment modality selected from endoscopic mucosal resection, endoscopic submucosal dissection, a therapeutically effective amount of radiofrequency ablation, a therapeutically effective amount of cryoablation, a therapeutically effective amount of photodynamic therapy and combinations thereof.

In some embodiments, the subject is assigned to the low mutational load risk category when the subject has a mutational load greater than 0.0 but less than or equal to 1.0. In some embodiments, the subject is assigned to the high mutational load risk category when the subject has a mutational load greater than 1.0.

In some embodiments, the subject is assigned to the low mutational load risk category when the subject has a mutational load greater than 0.0 but less than or equal to 1.5. In some embodiments, the subject is assigned to the high mutational load risk category when the subject has a mutational load greater than 1.5.

In some embodiments, the subject is assigned to the low mutational load risk category when the subject has a mutational load greater than 0.0 but less than or equal to 2.5. In some embodiments, the subject is assigned to the high mutational load risk category when the subject has a mutational load greater than 2.5.

In some embodiments, the subject is assigned to the low mutational load risk category when the subject has a mutational load greater than 0.0 but less than or equal to 3.0. In some embodiments, the subject is assigned to the high mutational load risk category when the subject has a mutational load greater than 3.0.

In some embodiments, the subject is assigned to the low mutational load risk category when the subject has a mutational load greater than 0.0 but less than or equal to 3.5. In some embodiments, the subject is assigned to the high mutational load risk category when the subject has a mutational load greater than 3.5.

In some embodiments, the subject is assigned to the low mutational load risk category when the subject has a mutational load greater than 0.0 but less than or equal to 4.0. In some embodiments, the subject is assigned to the high mutational load risk category when the subject has a mutational load greater than 4.0.

In some embodiments, the subject is assigned to the low mutational load risk category when the subject has a mutational load greater than 0.0 but less than or equal to a mutational load of about 0.1 to about 5.0. In some embodiments, the subject is assigned to the high mutational load risk category when the subject has a mutational load greater than between 0.1 and 5.0.

In some embodiments, the risk categories are selected from no mutational load, low mutational load, and high mutational load. In some embodiments, the subject is assigned to the no mutational load risk category when the subject has mutational load of 0.0. In some embodiments, no mutational load is indicative of no risk of disease progression from Barrett's metaplasia to esophageal adenocarcinoma. In some embodiments, no mutational load is indicative of the absence of actionable disease. In some embodiments, the absence of actionable disease is categorized as Barrett's metaplasia with a lower risk of progression than the baseline risk for Barrett's metaplasia, wherein surveillance of the patient can be safely discontinued.

In some embodiments, the subject is assigned to the low mutational load risk category when the subject has a mutational load greater than 0.0 but less than 1.75. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the low mutational load risk category when the subject has a mutational load greater than 0.0 but less than 2.0. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the high mutational load risk category when the subject has a mutational load greater than 2.0. In some embodiments, the subject is assigned to the high mutational load risk category when the subject has a mutational load greater than or equal to 2.0. In some embodiments, the wherein a high mutational load is indicative of high risk of disease progression from Barrett's metaplasia to esophageal adenocarcinoma. In some embodiments, a high mutational load is indicative of suitability of the subject for at least one treatment modality selected from endoscopic mucosal resection, radiofrequency ablation, cryoablation, endoscopic submucosal dissection, photodynamic therapy and combinations thereof.

In some embodiments, the subject is assigned to the low mutational load risk category when the subject has a mutational load greater than 0.0 but less than or equal to 1.75. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the low mutational load risk category when the subject has a mutational load greater than 0.0 but less than 1.75. In some embodiments, a low mutational load is indicative of a low risk of disease progression from Barrett's metaplasia to esophageal adenocarcinoma. In some embodiments, a low mutational load is indicative of suitability of the subject for monitoring.

In some embodiments, the subject is assigned to the high mutational load risk category when the subject has a mutational load greater than 1.75. In some embodiments, the subject is assigned to the high mutational load risk category when the subject has a mutational load greater than or equal to 1.75. In some embodiments, the wherein a high mutational load is indicative of high risk of disease progression from Barrett's metaplasia to esophageal adenocarcinoma. In some embodiments, a high mutational load is indicative of suitability of the subject for at least one treatment modality selected from endoscopic mucosal resection, radiofrequency ablation, cryoablation, endoscopic submucosal dissection, photodynamic therapy and combinations thereof.

In some embodiments, the pre-determined mutational load cut-offs are variable. In some embodiments, the subject is assigned to the low mutational load risk category when the subject has a mutational load greater than 0.0 but less than or equal to a mutation load ranging from about 1.75 to about 2.0. In some embodiments, the subject is assigned to the low mutational load risk category when the subject has a mutational load greater than 0.0 but less than a mutation load ranging from about 1.75 to about 2.0. In some embodiments, the subject is assigned to the high mutational load risk category when the subject has a mutational load greater from about 1.75 to about 2.0. In some embodiments, the subject is assigned to the high mutational load risk category when the subject has a mutational load greater than or equal from about 1.75 to about 2.0.

In some embodiments, the indication for a particular clinical management of a patient to prevent or eradicate cancer depends on the cost of the management, the risk of disease progression toward cancer, and the tolerability and side effects associated with that management choice.

In some embodiments, three types of options exist for the management of Barrett's esophagus: 1) Intervention aimed at disease eradication, 2) Endoscopic surveillance aimed at detecting disease before too much progression, and 3) No action (no surveillance or intervention).

In some embodiments, ML stratifies the risk of disease progression, and the cost of the intervention does not depend on the ML observed in the patient, the utility of ML in improving risk assessment for disease progression is the ability to intervene earlier in those patients that need it while sparing other patients intervention and allowing a reduction of surveillance in others.

In some embodiments, different ML levels would be associated with distinct clinical management strategies. In some embodiments, improves the estimation of risk of disease progression.

TABLE 2

Risk of progression and clinical management by ML level

| ML | Likelihood of Disease Progression (toward esophageal adenocarcinoma) | Supports this clinical management |
|---|---|---|
| High | Elevated (forecast >5% risk) | Disease eradication OR closer surveillance if subject is not a good candidate for therapy |
| Medium | Low (But Above Baseline: Forecast 1-2% risk) | Standard Interval Surveillance (per American College of Gastroenteroloigists, interval is 1-3 years depending on grade of dysplasia observed) |
| None | Baseline (<0.5% progression to cancer) | Reduced Surveillance (i.e. less frequently than would be done based on guidelines and/or other risk factors alone) |

In some embodiments, disease eradications include ablation (e.g. radiofrequency, cryotherapy, plasma/photodynamic therapy), esophageal mucosal resection, esophageal submucosal enucleation, and combinations thereof.

In some embodiments, the subject is a human. In some embodiments, the subject is a human diagnosed with Barrett's esophagus. In some embodiments, the biological specimen is a mucosal lining of the esophagus. In some embodiments, the biological specimen is representative of a disease region.

In some embodiments, amplifying DNA sequences comprises: selecting a primer pair corresponding to a specific microsatellite region; adding the primer pair to the DNA sequences; and performing quantitative polymerase chain reaction on the DNA sequences with the primer.

In some embodiments, detecting mutations comprises determining the sequence of the amplified DNA and comparing the amplified DNA to a known wild type control sequence for the specific microsatellite region and identifying differences between the sequence of the amplified DNA and the known wild type control sequence.

In some embodiments, the specific microsatellite regions are selected from 1p (CMM1, Lmyc), 3p (VHL, OGG1), 5q (MCC, APC), 9p (CDKN2A, CDKN2B), 10q (PTEN, MXI1), 17p (TP53), 17q (NME1), 18q (DCC), 21q, 22q (NF2) and combinations thereof.

In some embodiments, categorizing clonality of each mutation comprises assigning one of three categories selected from the group consisting of no clonality, low clonality and high clonality. In some embodiments, high clonality is assigned where loss of heterozygosity is present in greater than about 75% of DNA analyzed. In some embodiments, low clonality is assigned where loss of heterozygosity is present in about 50% to about 75% of DNA analyzed. In some embodiments, no clonality is assigned where loss of heterozygosity is present in less than about 50% of DNA analyzed.

In some embodiments, calculating the mutational load comprises assigning a score to each mutation based on a categorization of low or high clonality of each mutation, wherein the score for low clonality is 0.5x, wherein x is the number of low clonality mutations and the score for high clonality is y, wherein y is the number of high clonality mutations; and wherein the overall mutational load is y+0.5x. In some embodiments, mutation load can be expressed generally as $x*W_{Low}+y*W_{High}$, where $W_{Low}$ and $W_{High}$, are weightings for low and high clonality respectively.

In some embodiments, calculating the mutational load further comprises assigning a score to each mutation based on detection of DNA microsatellite instability at a particular locus, wherein DNA microsatellite instability at a single locus is defined as $0.75z$, wherein z is the number of loci displaying DNA microsatellite instability; wherein the score for low clonality is $0.5x$, wherein x is the number of low clonality mutations and the score for high clonality is y, wherein y is the number of high clonality mutations; and wherein the overall mutational load is $y+0.5x+0.75z$. In some embodiments, DNA microsatellite instability is determined by the presence of at least one of the shortening and lengthening of a DNA microsatellite region. In some embodiments, the emergence of new alleles, manifested as DNA microsatellite instability mutations" as this is the first MSI that has been seen in these markers.

In some embodiments, calculating the mutational load further comprises assigning a score to each mutation based on detection of DNA microsatellite instability at multiple loci, wherein DNA microsatellite instability at multiple loci is defined as $2z$, wherein z is the number of loci displaying DNA microsatellite instability; wherein the score for low clonality is $0.5x$, wherein x is the number of low clonality mutations and the score for high clonality is y, wherein y is the number of high clonality mutations; and wherein the overall mutational load is $y+0.5x+2z$. In some embodiments, DNA microsatellite instability is determined by the presence of at least one of the shortening and lengthening of a DNA microsatellite region. In some embodiments, the emergence of new alleles, manifested as DNA microsatellite instability mutations" as this is the first MSI that has been seen in these markers.

In some embodiments, calculating the mutational load further comprises assigning a score to each mutation based on detection of DNA microsatellite instability at multiple loci, wherein DNA microsatellite instability at multiple loci is defined as $1z$, wherein z is the number of loci displaying DNA microsatellite instability; wherein the score for low clonality is $0.5x$, wherein x is the number of low clonality mutations and the score for high clonality is y, wherein y is the number of high clonality mutations; and wherein the overall mutational load is $y+0.5x+1z$. In some embodiments, DNA microsatellite instability is determined by the presence of at least one of the shortening and lengthening of a DNA microsatellite region. In some embodiments, the emergence of new alleles, manifested as DNA microsatellite instability mutations" as this is the first MSI that has been seen in these markers.

In some embodiments, calculating the mutational load further comprises assigning a score to each mutation based on detection of DNA microsatellite instability at multiple loci, wherein DNA microsatellite instability at multiple loci is defined as $0.5z$, wherein z is the number of loci displaying DNA micro satellite instability; wherein the score for low clonality is $0.5x$, wherein x is the number of low clonality mutations and the score for high clonality is y, wherein y is the number of high clonality mutations; and wherein the overall mutational load is $y+0.5x+0.5z$. In some embodiments, DNA microsatellite instability is determined by the presence of at least one of the shortening and lengthening of a DNA microsatellite region. In some embodiments, the emergence of new alleles, manifested as DNA microsatellite instability mutations" as this is the first MSI that has been seen in these markers.

In some embodiments, calculating the mutational load further comprises assigning a score to each mutation based on detection of DNA microsatellite instability at a particular locus, wherein DNA microsatellite instability at a single locus is defined as $0.75z_1$, and wherein DNA microsatellite instability at multiple loci is defined as $0.5z_2$, wherein $z_1$ is the number of loci displaying DNA microsatellite instability and $z_2$ is the number of loci displaying DNA microsatellite instability greater than 1; wherein the score for low clonality is $0.5x$, wherein x is the number of low clonality mutations and the score for high clonality is y, wherein y is the number of high clonality mutations; and wherein the overall mutational load is $y+0.5x+0.75z_1+0.5z_2$.

In some embodiments, calculating the mutational load further comprises assigning a score to each mutation based on detection of DNA microsatellite instability at a particular locus, wherein DNA microsatellite instability at a single locus is defined as $0.75z_1$, and wherein DNA microsatellite instability at multiple loci is defined as $0.75z_1+0.5z_2$, wherein $z_1$ represent a single locus displaying DNA microsatellite instability and $z_2$ is the number of loci displaying DNA microsatellite instability greater than 1 locus; wherein the score for low clonality is $0.5x$, wherein x is the number of low clonality mutations and the score for high clonality is y, wherein y is the number of high clonality mutations; and wherein the overall mutational load is $y+0.5x+0.75z_1+0.5(z_2)$. In some embodiments $z_1=1$. By way of example, were 3 MSI mutations are detected, the above equation can be expressed as follows: mutational load=$y+0.5x+0.75(1)+0.5(2)$. Where a single MSI mutation is detected, the equation is expressed as follows: mutational load=$y+0.5x+0.75(1)$.

In some embodiments, calculating a mutational load further comprises summing the clonality weighting for each specific micro satellite region showing a mutation or DNA microsatellite instability.

In some embodiments, particular weightings may be assigned to a particular mutation, DNA microsatellite region or a combination thereof. In some embodiments, weightings are equal for all mutations in particular DNA microsatellite regions analyzed. In some embodiments, mutations in particular DNA microsatellite regions may be given higher weightings than other mutations in particular DNA microsatellite regions. In some embodiments, certain mutations in particular DNA microsatellite regions may have a greater influence on the ML for a particular subject. In some embodiments, mutations in particular DNA microsatellite regions may include, but are not limited to mutations in 17p (TP53) and 9p (CDKN2A, CDKN2B).

In some embodiments, calculating a mutational load further comprises assigning a distinct weighting for a mutation depending on the genomic locus of the mutations. Thus a low clonality mutation at 17p (TP53) or 9p (p16) may be weighted as 0.55 up to 0.75 rather than 0.5, and a high clonality mutation may be weighted as 1.05 up to 1.5.

In some embodiments, analysis of clonal diversity can supplement the embodiments described herein. In some embodiments, clonal diversity can in addition to the embodiments described herein serve as a factor in the prediction of disease progression.

In some embodiments, determining mutational load as a predictor of disease progression is independent of a histological standard.

This invention and embodiments illustrating the method and materials used maybe further understood by reference to the following non-limiting examples.

EXAMPLES

Example 1

The objective of mucosa ablation techniques in Barrett's esophagus is to eradicate mutation bearing intestinalized mucosa cells and induce their replacement by normal squamocolumnar lining cells. Mutational analysis was integrated into microscopic evaluation to better understand the biology of the mucosal ablative approach and to personalize the diagnosis and predict treatment efficacy.

Recut microscopic sections (4 um thick) from tissue blocks of 21 patients undergoing radiofrequency mucosal ablation (RMA) for Barrett's metaplasia and low-grade dysplasia were microdissected at multiple target sites. 16 patients underwent a single RMA and 5 were treated twice with histopathology available pre and post treatment for up to a 2.5-year follow-up. A total of 51 microdissection targets were analyzed for a broad panel of 16 allelic imbalance (loss of heterozygosity [LOH]) mutational markers affecting 1p, 3p, 5q, 9p, 10q, 17p, 17q, 18q, 21q, 22q using quantitative fluorescent PCR/capillary electrophoresis. The presence, cumulative number and extent of clonal expansion (% of microdissected target cells bearing individual mutations; less than 75%=lowly expanded mutations, greater than 75%=high) was correlated with the histopathologic features.

RMA induced replacement of Barrett's metaplasia by normal mucosa in 15 or 16 patients (94%). In each case, mutations that were present in the metaplastic cells were no longer detectable in post-ablative specimens indicating that the mutated clone and its precursors had been eradicated. In the one patient with persistent disease, all mutations that were shown to be lowly clonally expanded were eradicated but the highly expanded mutations remained. Similarly, in patients requiring two RMA procedures, highly clonally expanded mutations remained present in intestinalized cells after initial treatment. Such highly expanded mutations were seen to affect a wide range of markers and were not confined to a single genomic locus. Of note, mutational regression did not necessary take place immediate after treatment but could occur at 6-12 months.

RMA is shown to induce regression of mutation bearing and cause reversion of intestinalized to normal squamocolumnar cells. Regression is time dependent and can occur at 6-12 months following treatment. Intestinalized mucosal cells bearing highly clonally expanded mutations are more resistant to regression but can be eliminated by repeat treatment. Integrated microscopic/molecular analysis provides sensitive parameters with which to classify, plan RMA and monitor patient with Barrett's metaplasia on a more personalized basis.

Example 2

True low-grade dysplasia of the esophagus confers an increased risk of development of adenocarcinoma of 5 times relative to those without dysplasia. However, microscopic discrimination between intestinal metaplasia and low-grade dysplasia can be challenging.

Barrett's specimens from 215 patients were microdissected into 420 distinct targets comprising disease states of columnar (non-Barrett's) metaplasia, intestinal (Barrett's) metaplasia, low-grade dysplasia, and high-grade dysplasia. Microdissection targets were tested for loss of heterozygosity in a panel of 16 microsatellite markers using PCR/capillary electrophoresis. The presence or absence of mutation and the proportion of cells affected by mutation were quantitatively determined, with high clonality mutations representing >75% of cells, and low clonality representing 50%-75%. Numbers of high and low clonality mutations were fit to disease state using proportional odds logistic regression.

There was a significant relationship between disease state and number and clonality of mutations, with high clonality mutations weighted approximately twice as much as low clonality. A regression score of 5.3 or greater, corresponding to 2 or more high clonality mutations discriminated low-grade dysplasia from metaplasia. Similarly, a score of 7.9 or greater, corresponding to approximately 3 high clonality mutations, discriminates high grade from low-grade dysplasia.

TABLE 3

Number of mutations and regression results

| Disease State | Mutations | | | Score |
|---|---|---|---|---|
| | Low | High | Total | |
| Columnar Metaplasia | 0.6 (0-3) | 0.0 (0-1) | 0.6 (0-3) | 0.75 (0-3.6) |
| Intestinal Metaplasia | 1.2 (0-5) | 0.3 (0-2) | 1.5 (0-5) | 2.15 (0-6.0) |
| Low Grade Dysplasia | 2.6 (1-5) | 0.8 (0-3) | 3.4 (1-5) | 4.9 (1.16-9.6) |
| High Grade Dysplasia | 1.4 (0-5) | 2.6 (1-3) | 4 (3-6) | 7.9 (4.7-9.6) |

Molecular profiling of Barrett's esophagus can serve as a useful adjunct to histopathologic interpretation in determining the presence and grade of dysplasia.

Example 3—Evaluating Mutation Load in Low and High Grade Dysplasia in Barrett's Esophagus A panel of molecular markers was evaluated to analyze the overall degree of molecular change in conjunction with histologic diagnosis.

Methods:

20 biopsy specimens from patients with a pre-established diagnosis of dysplasia (n=19) and intestinal metaplasia (n=1) were examined. Multiple targets (n=57) from formalin-fixed, paraffin-embedded slides were microdissected and tested for LOH mutations and/or microsatellite instability in a panel of 17 microsatellite markers using PCR and capillary electrophoresis. The presence or absence of LOH and the proportion of cells affected by LOH were quantitatively determined, with high clonality mutations representing >75% of cells, and low clonality representing 50-75%. We estimated mutation load using numbers of low and high clonality mutations and the number of loci affected by microsatellite instability.

Results:

Microdissection targets with histologic HGD (range 2.0-6.0, average 3.3) had higher mutation load than LGD (range 1.50-4.5, average 2.4). Targets with carcinoma in situ (CIS) showed significantly higher mutational load (range 3.0-7.0, average 5.3) than targets showing only high-grade dysplasia. 30% of HGD targets had mutation loads in the range associated with LGD (i.e., below average for HGD). Likewise, 33% of LGD targets had mutation loads associated with IM.

Conclusions:

Molecular profiling of BM, with mutation load determination, can serve as a useful adjunct to histologic interpretation in determining the presence and degree of dysplasia, and may help clarify the potential for biologic aggressiveness within a particular BM specimen.

Example 4—Evaluation of Mutational Load (ML) in Microdissection Target of Dysplastic and Non-Dysplastic Barrett's Esophagus Methods:

We examined biopsy specimens from 59 patients with BM. Patients were 30 to 88 years of age (mean 60 years), with 47 males and 12 females. Mean BM segment length was 2.8 cm. We microdissected multiple targets (n=146) from biopsy slides and tested them for loss of heterozygosity (LOH) and/or microsatellite instability (MSI) in a panel of 17 microsatellite markers targeting known tumor suppressor genes. The presence or absence of LOH and the proportion of cells affected by LOH were quantitatively determined, with high clonality mutations representing >75% of cells, and low clonality representing 50%-75%. We estimated ML using numbers of low and high clonality mutations and the number of loci affected by MSI. Individual targets were then independently diagnosed histologically by 3 pathologists blinded to molecular findings.

Results:

Increased ML correlated with increasing severity of disease according to consensus diagnosis (Table 4), (p<0.0001). There was consensus diagnosis in $130/146$ targets (3-way in 82 targets and 2-way in 48). Concordance of diagnosis was higher for histologic diagnosis of the whole slide than for individual targets (kappa=0.5 for whole slide vs. 0.3 for individual targets). Of 110 targets with IM-only, 35 (27%) had No ML (no mutations), 70% had Low ML (0<ML<=2), and (3) 3% had High ML (ML>2). These percentages were similar to previously reported results. 2 of 4 targets histologically diagnosed as HGD/CIS had High ML, and 2 had Low ML. Notably, several cases with HGD/CIS consensus diagnosis had lower grades of disease described in their original pathology report.

TABLE 4

Summary of mutational load by histological diagnosis

| Histologic Diagnosis | # Targets | Mutational Load | |
| --- | --- | --- | --- |
| | | Average | Range |
| Intestinal Metaplasia | 110 | 0.8 | 0-2.5 |
| Indeterminate for Dysplasia | 9 | 0.5 | 0-1.5 |
| Low Grade Dysplasia | 7 | 2.0 | 0.8-5.0 |
| High Grade Dysplasia/CIS | 4 | 2.5 | 1.5-4 |

Conclusions:

Severity of histologic diagnosis in BM correlates with ML. A subset of IM with no histologic features of dysplasia had High ML, which correlates with high-grade dysplasia. Determining ML may assist in risk-stratification to determine which patients should be treated more aggressively and which should have surveillance.

Example 5—Correlation of the Presence and Extent of Loss of Heterozygosity Mutations with Histological Classifications of Barrett's Esophagus At present, there are no observable microscopic features of metaplasia that can determine if BM is likely to undergo disease progression to cancer or remain stable. The limited ability of histological features alone to identify those intestinal metaplasia cases likely to progress has led many to consider ablation and other interventions at the earliest stage of BM. This increased use of ablation has raised concerns over the associated healthcare economic burden. Thus, supplementary diagnostic modalities that help to better characterize the early stages of disease would be a valuable addition to personalizing patient treatment and controlling these healthcare costs.

The aim of this study was to better understand the relationship between histological changes in BM and mutation acquisition by comparing cumulative gene mutation information of specific cell populations to their histological classification. Previous work using microdissection-guided broad panel profiling for LOH mutations in proximity to tumor suppressor genes has shown clinical utility for a variety of cancer applications. This method was employed to characterize multiple sites within esophageal biopsy specimens from patients with BM. Cell populations with various histological classifications were tested for LOH across a panel of relevant genomic loci in order to characterize the overall LOH mutational load next to tumor suppressor genes. It was hypothesized that increasing mutational loads would correlate with increasingly severe histological classifications of BM. We show that an analytically objective and reproducible measure of genomic instability, as assessed by mutational profiling of clonally expanded cell populations, can assist histology in the characterization of BM.

Methods

Study Cohort

Standard histological sections (4 μm thick) of archival, formalin-fixed, paraffin-embedded (FFPE) from 271 patients histologically known to have BM tissue were microscopically reviewed. Patients in the study cohort had previously undergone upper GI endoscopy and pathology review of biopsy specimens. Patients with a histological classification of intestinal metaplasia, "indefinite for dysplasia", and various grades of dysplasia were selected for inclusion in the study. Patients without evidence of BM were excluded, as were patients with intramucosal and/or invasive carcinoma.

Microdissection

Hematoxylin and eosin (H&E) stained, formalin-fixed, paraffin embedded (FFPE) slides were used to guide microdissections of histologically classified targets from 6-8 unstained, serial FFPE slides. Multiple distinct regions were microdissected from each slide to obtain cells corresponding to distinct foci of histologically classified disease. Multiple targets were taken according to the availability of topographically separate tissue fragments, even when these fragments were from the same histological classification of BM (FIG. 1). Microdissections typically resulted in 3-8 targets for a given slide (FIG. 1). Separate microdissected targets of histologically classified normal squamous epithelium and epithelium containing columnar cells that were not intestinalized (e.g., normal squamous and non-Barrett's columnar mucosa) were examined as a baseline control for mutational markers. These targets were microdissected from the same FFPE slides as targets with various histological classifications of BM. Accuracy of microdissection was confirmed by microscopic review of post-microdissection stained slides.

Histological Classification

A histological classification for each target was assigned based on review of the specimens and accompanying histopathology reports from the original microscopic review. When consensus between pathologists was available, it was used as the histological classification for the target. When consensus was not available, we relied on the histological classification of the expert pathologist in our group. Targets were classified as non-Barrett's epithelium and Barrett's epithelium using the following histological classifications in order of increasing severity: normal squamous and columnar mucosa for non-Barrett's epithelial targets, and intestinal metaplasia, "indefinite for dysplasia", LGD, and HGD for Barrett's epithelial targets.

Detection of LOH

LOH at 10 separate genomic loci using a panel 16 LOH markers associated with common tumor suppressor genes relevant to BM were assessed using PCR and quantitative capillary electrophoresis. The panel contained markers at the following chromosomal loci (associated genes in parenthesis): 1p (CMM1, L-myc), 3p (VHL, HoGG1), 5q (MCC, APC), 9p (CDKN2A), 10q (PTEN, MXI1), 17p (TP53), 17q (NME1), 18q (DCC), 21q (TFF1 and PSEN2) and 22q (NF2). Marker qualification studies were performed using surgically resected EA specimen's microdissected at sites of intestinal metaplasia, dysplasia, and EA, with histological classification at each site representing consensus of four GI pathologists. In that study, numerous genomic loci adjacent to tumor suppressor genes were analyzed for LOH. The results of such studies were used to select a smaller, more relevant panel of genomic loci to examine. The smaller panel used here was limited to LOH mutational markers next to tumor suppressor genes with a mutation in at least 20% of the surgical EA specimens.

Normal variability was characterized in preliminary studies for each pairing of allele lengths examined for LOH in order to account for differing nucleic acid amplifications related to differences in allele length. Normal squamous, non-Barrett's epithelial targets were used to characterize this variability. By analyzing this variability, it was possible to quantitatively estimate the proportion (clonality) of cells mutated at a particular genomic locus. Each microdissected target was tested for each molecular marker in duplicate or triplicate in order to ensure reproducibility. Mutational profiles in cell populations were defined as high clonality when >75% of the DNA was mutated and low clonality when 50-75% of the DNA was mutated. When <50% of the DNA was mutated, no mutations were reported due to the analytical limit of detection of the assay, which was 50% for each LOH.

Mutational Load

For each microdissected target, the total number of mutations, the number of low clonality mutations, and the number of high clonality mutations were determined. Proportional odds logistic regression (POLR) was used to define weights for numbers of low and high clonality mutations and produce an estimate of mutation load (ML). In performing POLR, various histological classifications of epithelia were grouped together (e.g. non-BM epithelium vs. intestinal metaplasia vs. LGD vs. HGD, including or excluding "indefinite for dysplasia" targets, or all non-dysplastic vs. dysplastic, etc.) to determine the impact on the calculated weightings. Weightings were also evaluated using fractional allelic loss (FAL), an analysis for the proportions of low and high clonality mutations to the number of informative markers. All results from various analyses consistently determined a weight of 0.5 for low clonality mutations and 1 for high clonality mutations.

The correlation between histological class and mutational load using was examined using a Spearman rank correlation and calculated frequency distributions for each histological class within the study population. Levels of mutational load were established based on the frequency with which a particular level of mutational load was observed in targets histologically classified as intestinal metaplasia. The no mutational load level consisted only of intestinal metaplasia targets that lacked detectable mutations. The high ML level was defined as the level that captured 5% of intestinal metaplasia targets that had the highest level of ML. However, because ML was defined at discrete levels, only 4% of intestinal metaplasia targets were included by this cutoff. The low ML level included all intestinal metaplasia targets that had mutations but had an ML below the high ML cutoff. We used these levels of mutational load to evaluate the mutational load in other histological classifications. The frequency of mutations in various genomic loci of each target was also determined for each histological class.

Results

LOH Mutational Analysis

Esophageal biopsies were examined for LOH mutational profiles adjacent to tumor suppressor genes. Each FFPE biopsy slide was microdissected at multiple target sites as guided by histologically observed cellular morphology (FIG. 1). Microdissections of distinct targets were performed on patient samples with various demographics (Table 5). There were 199 males and 72 females from which 568 distinct microdissection targets were analyzable.

TABLE 5

Demographics of patients included in study

| Age (years) | Male | Female | Total |
| --- | --- | --- | --- |
| <40 | 8 | 2 | 10 |
| 40-50 | 31 | 13 | 44 |
| 50-60 | 54 | 26 | 80 |
| 60-70 | 59 | 14 | 73 |
| 70-80 | 33 | 10 | 43 |
| ≥80 | 14 | 7 | 21 |
| Total | 199 | 72 | 271 |

The number of LOH mutations was determined in targets with various histological classifications. Table 6 summarizes the number of mutated LOH loci per microdissected target averaged for all targets across the range of histological classes examined. The number of mutated LOH loci increased with increasing severity of histological classification. Most LOH mutations were detected in HGD targets, and in those HGD targets a relatively high proportion of cells were found with these mutations (high clonality). While most mutations found in HGD targets were high clonality, mutations found in non-dysplastic histological classifications (intestinal metaplasia, "indefinite for dysplasia") were typically low clonality. There were less mutations detected in targets histologically classified as normal squamous epithelium and epithelium containing columnar cells that were not intestinalized (columnar, non-Barrett's epithelium). Importantly, there were no high clonality mutations found in targets with these histological classifications (Table 6).

TABLE 6

Summary of total mutations detected by each histological classification

| Histological Classification | Total Targets Tested | Average number of mutated loci detected per microdissected target | Average number of Low/High Clonality mutations detected per microdissected target | | Average Mutational Load |
|---|---|---|---|---|---|
| | | | Low | High | |
| Normal Squamous | 82 | 0.1 | 0.1 | 0.0 | 0.1 |
| Columnar | 77 | 0.6 | 0.6 | 0.0 | 0.3 |
| Intestinal Metaplasia | 216 | 1.5 | 1.2 | 0.3 | 0.9 |
| Indefinite for dysplasia | 138 | 2.0 | 1.7 | 0.3 | 1.1 |
| Low grade dysplasia | 39 | 3.5 | 2.7 | 0.8 | 2.2 |
| High grade dysplasia | 16 | 4.0 | 1.5 | 2.5 | 3.3 |

Mutations were observed across the entire panel of genomic loci examined. Table 7 summarizes the frequency of mutation in each genomic loci for each histological class. Targets histologically classified with dysplasia had the highest frequency of mutations at 17p (TP53), with mutations present in $14/16$ (88%) HGD targets, $27/39$ (69%) LGD targets, and $49/138$ (36%) "indefinite for dysplasia" targets. 9p (CDKN2A) was also more frequently mutated than other loci with $7/16$ (47%) HGD targets, $20/39$ (51%) LGD targets, and $45/138$ (33%) "indefinite for dysplasia" targets displaying mutations.

Assessment of Genomic Instability

Mutational load (Table 6, FIG. 2) represents tumor suppressor gene LOH mutations within clonally expanded cell populations in microdissected targets. Higher clonality mutations were indicative of a greater number of cells with the same mutations within a microdissected target. Semi-quantitative analysis was used that incorporated the number of mutations and the proportion of cell populations that had mutations to assess mutational load. In this system, low clonality mutations were weighted with a numerical value of 0.5 and high clonality mutations with a value of 1 in order to determine the overall LOH mutational load for each target.

Figure 2:
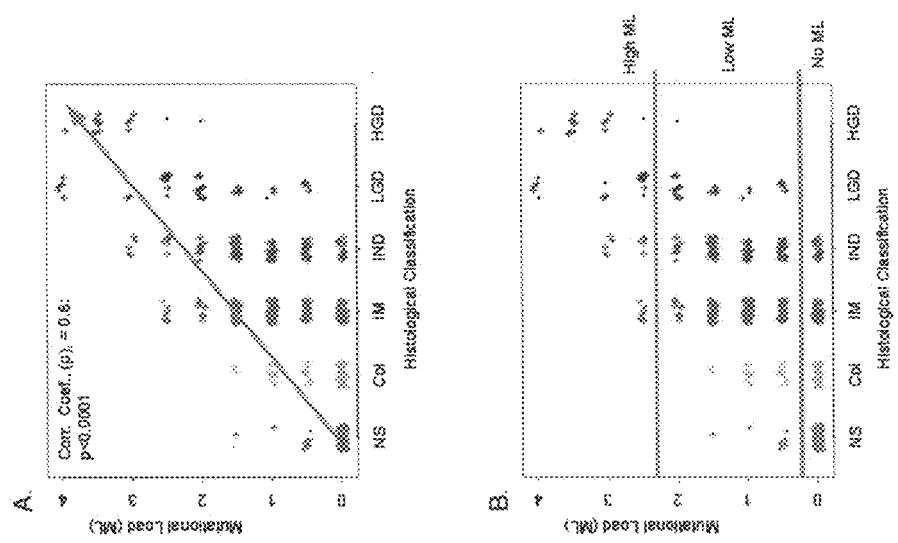
FIG. 2 depicts mutational load (ML) in microdissected targets by histological classification. A.) There was a statistically significant correlation between increasingly severe histological classification and increasing mutational load (correlation coefficient, ($\rho$), =0.6; p<0.0001). B.) Levels of mutational load (no ML, low ML, and high ML) were established within targets histologically diagnosed as intestinal metaplasia and then applied to other histological classifications. NS=normal squamous epithelium; Col=columnar, non-Barrett's epithelium; IM=intestinal metaplasia; IND="indefinite for dysplasia"; LGD=low-grade dysplasia; and HGD=high-grade dysplasia.

The mutational load for each microdissected target was correlated to the histological class of the target (FIG. 2). For each target, mutational load was positively correlated to histological classification, with the overall number and clonality of mutations increasing with increasingly severe histological classification (FIG. 2A). Using the frequency with which mutational load was observed in intestinal metaplasia we established three levels of Mutational Load (ML) with respect to each histological classification (FIG. 2B). The first level contained targets that lacked mutations and, as such, had no detectable ML. The second level contained targets with 1 low clonality mutation to 2 high clonality mutations with a mutational load greater than 0 but less than or equal to 2 and was defined as having low ML. The third level contained targets with greater than two high clonality mutations with a mutational load greater than 2 and was defined as having high ML.

Table 5 summarizes the proportion of microdissected targets for each level of mutational load in each histological class. The majority of histological targets with normal squamous epithelium and epithelium containing columnar cells that were not intestinalized (90% of normal squamous epithelial targets and 61% of columnar, non-Barrett's epithelial targets) had no detectable ML (Table 8). Of the proportion of squamous and columnar targets that had mutations, all were low clonality mutations falling into levels of low ML (Table 6). 22% of histologically diagnosed intestinal metaplasia targets and 14% of "indefinite for dysplasia" targets had no ML, while the remaining proportion of intestinal metaplasia and "indefinite for dysplasia" targets had mutations. All targets histologically classified as HGD and LGD had mutations with all targets falling into the low ML or high ML levels. All but one HGD target was characterized having high ML. Comparatively, only 4% of intestinal metaplasia and 9% of "indefinite for dysplasia" targets were characterized as having a high ML.

TABLE 7

Frequency of LOH mutations adjacent to tumor suppressor genes were examined by histological classifications

| | | Percent of mutated markers in each histological classification | | | | | |
|---|---|---|---|---|---|---|---|
| Loci | Tumor suppressor genes | Normal squamous N = 82 | Columnar N = 77 | Intestinal metaplasia N = 216 | Indefinite for dysplasia N = 138 | Low grade dysplasia N = 39 | High grade dysplasia N = 16 |
| 1p | CMM1, LMYC | 1 | 0 | 13 | 20 | 11 | 5 |
| 3p | VHL, OGG1 | 1 | 4 | 29 | 24 | 20 | 8 |
| 5q | MCC, APC | 2 | 8 | 43 | 25 | 11 | 13 |
| 9p | CDKN2A | 4 | 4 | 56 | 45 | 20 | 7 |
| 10q | PTEN, MXI1 | 0 | 11 | 54 | 40 | 12 | 2 |
| 17p | TP53 | 1 | 4 | 35 | 49 | 27 | 14 |
| 17q | NME1 | 1 | 7 | 21 | 33 | 17 | 9 |
| 18q | DCC | 1 | 7 | 41 | 14 | 12 | 4 |
| 21q | TFF1, PSEN2 | 0 | 3 | 20 | 18 | 7 | 0 |
| 22q | NF2 | 0 | 0 | 11 | 3 | 0 | 2 |

Bold numbers indicate that at least 25% of targets tested with each histological classification had the indicated LOH mutations.

TABLE 8

Frequencies of mutational load (ML) in targets by histological classification

| Histological classification of microdissected targets | Level of Mutational load (ML) | | |
|---|---|---|---|
| | No ML | Low ML (1 low clonality- 2 high clonality) | High ML (>2 high clonality) |
| Normal squamous | 74 (90%) | 8 (10%) | 0 (0%) |
| Columnar | 47 (61%) | 30 (39%) | 0 (0%) |
| Intestinal metaplasia | 48 (22%) | 159 (74%) | 9 (4%) |
| Indefinite for dysplasia | 20 (14%) | 106 (77%) | 12 (9%) |
| Low grade dysplasia | 0 (0%) | 22 (56%) | 17 (44%) |
| High grade dysplasia | 0 (0%) | 1 (6%) | 15 (94%) |

Discussion

Accumulation of genomic instability within and next to oncogenes and tumor suppressor genes drives unregulated cell growth that can result in expansion of clonal cell populations and, ultimately, progression to cancer. In this study, genomic instability was surveyed by assessing LOH mutations adjacent to tumor suppressor genes across cell populations with a range of histological classifications. The presence and extent of LOH mutations in cell populations was correlated to each histological class. Microdissected targets, guided by morphological features, were taken at multiple sites, as available, in biopsy specimens. The overall number of mutations and clonality of cells with mutations were formulated into a mutational load that increased in correlation with increasingly severe histological classification. This correlation is consistent with the known fact that increasing genomic instability drives clonal expansion of cells and disease progression in BM.

BM targets with a histological classification of intestinal metaplasia were used to define three levels of Mutational Load (ML) with respect to each histological class: no ML, low ML and high ML (FIG. 2B, Table 7). Levels of mutational load in tumor suppressor genes were established with respect to specimens histologically classified with intestinal metaplasia because i) the presence of intestinal metaplasia can be relatively reliably diagnosed; and, ii) intestinal metaplasia is more prevalent in the clinical population than more severe histological classes of BM. Therefore, defining levels of mutational load with respect to intestinal metaplasia makes the levels most relevant to the most frequent and reliable histology found in patients with BM. Targets with no ML were found in non-dysplastic histological classifications. Targets with low ML had relatively low levels of LOH mutational accumulation without evidence of clonal expansion of mutated cells. Targets with high ML had relatively high levels of LOH mutational load and clonal expansion of cells with these mutations. High ML was consistently found in higher levels of histological dysplasia; however, high ML was also seen in some cases with less severe histological classifications, such as intestinal metaplasia.

Specimens histologically classified as intestinal metaplasia and "indefinite for dysplasia" spanned a similar spectrum of LOH mutational load (no ML through high ML). We found that 78% of intestinal metaplasia targets had detectable mutations, despite the absence of morphological changes indicative of dysplasia. These results are consistent with a large body of work suggesting that DNA alterations in BM precede the overt morphological development of dysplasia. Inflammatory responses can produce cellular changes that overlap those seen in true, confirmed histological dysplasia making differentiation of reactive atypia from true dysplasia difficult to determine. "Indefinite for dysplasia" targets tended to have higher mutation load than those with intestinal metaplasia, with mutations detected in 86% of targets (Table 8). Since these targets were histologically indefinite, some may, in fact, have more advanced mutational damage than others. As with intestinal metaplasia, some "indefinite for dysplasia" targets may have mutations that precede morphological changes consistent with dysplasia. Therefore, mutational analysis may provide additional information to aid in clinical diagnosis and management when such microscopic changes have yet to occur or are indefinite.

Lack of mutations (no ML) was observed in targets histologically classified as normal squamous epithelium and epithelium containing columnar cells that were not intestinalized (90% of normal squamous epithelial targets; 61% of columnar, non-Barrett's epithelial targets) and in some of those classified with intestinal metaplasia (22%) and "indefinite for dysplasia" (14%) (Table 8). This lack of mutations (no ML) was not detected in any targets with histological dysplasia. In previous studies across other organ groups using a similar LOH panel to examine mutations located near tumor suppressor genes, cell populations that lacked detectable LOH mutations were strongly correlated with benign, reactive processes. Although gene panels employed in this study and previous ones are not a complete examination of the entire genome, the absence of clonally expanded cells with LOH mutations next to the large number of tumor suppressor genes surveyed in our panel is strong evidence that the disease does not have extensive genomic instability. Therefore, targets that lack mutational load (no ML) are likely in the very early stages of neoplastic development or are morphologically displaying benign, reactive processes.

Targets that displayed low ML and were histologically classified as normal squamous epithelium and epithelium containing non-intestinalized columnar cells (10% of normal squamous epithelial targets; 39% of columnar, non-Barrett's epithelial targets) could represent actual mutations within histologically normal appearing mucosa or detection of mutated DNA from adjacent cells or intercellular fluids. The squamous and columnar mucosal targets were microdissected from the same FFPE biopsy slides as those histologically diagnosed with BE, making it possible that mutations from the adjacent Barrett's epithelium or intercellular fluids were detected. The mutational load in these squamous and columnar epithelial targets could also represent chromosomal aberrations that have yet to become morphologically visible by histology.

HGD is considered a severe premalignant event that requires clinical intervention, because it is associated with greater risk of progression to EA. In our study, applying cutoffs derived from intestinal metaplasia targets classified all but one HGD target as having high ML. This supports the association of high levels of genomic instability with more severe histological classifications of BM and is in line with the concept that patients with high ML may also be at greater risk of progression to EA. Consistently, the presence of three or more DNA abnormalities in patients has been associated with a greater risk of progression towards cancer. High ML may, therefore, provide support for associated interventions, even when histological classification of BM may be less than severe dysplasia (intestinal metaplasia, "indefinite for dysplasia", LGD). High ML in less severe histological classifications of BM may be indicative of impending morphological changes that have yet to become histologically visible.

This study is consistent with others that have described LOH mutations adjacent to TP53 and CDKN2A tumor suppressor genes, which together have been associated with greater risk of BM progression to cancer. When LOH mutations next to these genes have been analyzed in combination with additional DNA molecular markers for genomic instability, the risk of progression increases by over 4 fold at 10 years (relative risk of 38.7). Similar to these studies, we examined the mutational load in cell populations using a diverse DNA molecular panel to assess genomic instability. LOH adjacent to TP53 and CDKN2A tumor suppressor genes were included in our panel and were found most frequently in targets with dysplasia (Table 7). Also included in our panel were 12 additional LOH markers next to other tumor suppressor genes relevant to BM and EA. Mutations were found in every one of the LOH markers in our panel (Table 7). Furthermore, the number of cells with each LOH mutation (clonality of LOH) was also assessed (Table 7). Increasing sizes of clones with genomic instability have been associated with increased risk of progression to EA. Consistently, the mutational load, which incorporates both the number and clonality of mutations, increased with increasingly severe histological class of BE, suggesting that mutational load is a relevant measure of genetic damage that can provide additional, objective information to the existing histological classification.

In addition to enhancing histological classification, this type of mutational profiling may also facilitate monitoring using sequential biopsies taken over varying periods of time prior to determining if ablation is needed. Furthermore, it can provide objective molecular information with respect to the success of ablation. As with other forms of neoplasia, distinct clones of disease acquire distinct mutations, and a new clone is unlikely to have the same mutational profile as an existing clone. Incomplete elimination of the original clonal cell populations would be reflected in the same mutations persisting after ablation. In contrast, when the mutational profile in follow up biopsies differs from that of the initial biopsy, new clones of cells, as identified by different mutations, have likely evolved. When there is no evidence of mutations in follow up biopsies, complete eradication of atypical clones has likely been achieved.

A chief limitation in this study and all studies of BM is the variability associated with histological classification and the resulting lack of standardized histological classes for comparison to molecular results. Another limitation of this study concerns specimen type. Histology slides from biopsies are valuable specimens for studies such as this one, as they represent "real-world" specimens. However, biopsies are subject to sampling variation because, although current guidelines call for four-quadrant biopsies every 1 cm across the region of dysplastic BE, in clinical practice, more limited sampling often occurs.

Conclusions

The results of this study support the combined use of histological classification and mutational analysis to better evaluate BM.

This study demonstrates that various levels of mutational load (no ML, low ML, and high ML) adjacent to tumor suppressor genes exist within each histological classification (intestinal metaplasia, "indefinite for dysplasia", LGD, HGD). HGD consistently has high ML, while other less severe histological classifications have a heterogeneous range of ML, spanning from no ML through high ML. According to the American Gastroenterological Association technical review of BM management, when initial biopsy specimens histologically show no dysplasia, indefinite dysplasia, or LGD, risk stratification for BM progression to EA may be determined from collective clinical information, including the combined use of histological assessment and molecular biomarker information, if/when appropriate. Assessment of biopsy specimens for levels of mutational load using our panel of molecular markers provides a relevant, objective, and reproducible measure of mutational change that may serve as a useful adjunct to histopathology for determining appropriate patient management.

Example 6—Evaluation of Mutational Load in Microdissection Target of Dysplastic and Non-Dysplastic Barrett's Esophagus The aim of this study was to examine the relationship between mutational load (ML) and the histological classifications of BE FFPE biopsies of 59 patients yielded 146 targets that were classified as intestinal metaplasia (IM), indefinite for dysplasia (IND), low grade dysplasia (LGD) or high grade dysplasia (HGD) by 3 pathologists blinded to molecular results. Consensus diagnosis was defined as agreement between at least 2 pathologists. Targets were microdissected and analyzed for loss of heterozygosity (LOH) mutations using a panel of 16 DNA markers.

Table 9 shows the frequency of pathologist agreement on histological classification. At least one pathologist disagreed the majority of the time for IND (95%) and LGD (88%) classifications.

TABLE 9

Frequency of pathologist agreement on histological classification

|  | All Agree | 1 Disagrees | All disagree |
| --- | --- | --- | --- |
| IM | 79 (69%) | 35 (30%) | 1 (1%) |
| IND | 0 | 12 (63%) | 7 (37%) |
| LGD | 1 (13%) | 7 (88%) | 0 |
| HGD | 2 (50%) | 2 (50%) | 0 |

Conclusions: Increasing ML correlates with increasingly severe histological classifications. HGD frequently has a high ML, while other less severe histological classifications have a heterogeneous range of ML. Assessment of biopsy specimens for levels of ML provides a relevant, objective measure of genomic instability. This cohort had a distribution of no ML in IM targets consistent with previous studies (27% no ML, 70% low ML, 3% high ML) VERSUS (22% no ML, 74% low ML, 4% high ML). Combining the additional dimension of ML with histological classification helps to effectively risk stratify patients.

Example 7—Evaluation of Mutational Load (ML) in Four Independent Data Sets with Dysplastic and Non-Dysplastic Barrett's Esophagus Biopsy specimens from 370 patients with BE were microdissected into 787 distinct targets based on histological features from 4 independent study cohorts. Each target was histologically classified as intestinal metaplasia (IM), indefinite for dysplasia (IND), low grade dysplasia (LGD), high grade dysplasia (HGD), or carcinoma in situ (CIS). Each microdissection target was tested for loss of heterozygosity (LOH) and/or microsatellite instability (MSI) in a panel of 22 markers targeting known tumor suppressor genes using PCR/capillary electrophoresis. The presence or absence of LOH and/or MSI and the proportion of DNA affected by LOH mutation (clonality) were quantitatively determined. High clonality LOH mutations contained >75% of mutated DNA and low clonality LOH contained 50%-75%. Mutational load (ML) was estimated using the number of low and high clonality mutations and the number of loci affected by MSI.

Results: Increasing ML was found to consistently correlate with increasingly severe histology. Histological targets were classified as having no, low, or high ML. The no ML level consisted only of intestinal metaplasia microdissected targets that lacked detectable mutations. The high ML level was defined as the level that captured 5% of intestinal metaplasia microdissected targets that had the highest level of ML. The low ML level included all intestinal metaplasia microdissected targets that had mutations but had an ML below the high ML cutoff. Table 11 describes the percentage of microdissected targets with the indicated histology that had each level of ML. HGD and CIS frequently had high ML, while other less severe histological classifications had a heterogeneous range of ML.

TABLE 10

Percentage of microdissected targets in each histological class vs. level of ML

| Histological Diagnosis of Microdissected Targets | Level of Mutational Load (ML) | | |
|---|---|---|---|
| | No ML | Low ML | High ML |
| Non-BE | 76% (121) | 24% (38) | 0% (0) |
| Intestinal Metaplasia | 24% (82) | 67% (231) | 9% (32) |
| Indefinite for Dysplasia | 17% (25) | 67% (99) | 16% (23) |
| Low Grade Dysplasia | 0% (0) | 3% (22) | 68% (46) |
| High Grade Dysplasia | 0% (0) | 4% (2) | 96% (49) |
| Carcinoma in situ | 0% (0) | 0% (0) | 100% (17) |

Conclusions: Assessment of patients for levels of ML provides a relevant, objective measure of the presence and extent of genomic instability, which has been associated with BE disease progression.

Example 8—A Preliminary Longitudinal Assessment of Mutational Load in Patients with Barrett's Esophagus Risk stratification of BE for progression to EA relies on histological classification of dysplasia. However, histology alone cannot effectively risk stratify non-dysplastic BE. Progression of BE neoplasia is associated with accumulation of genomic instability and clonal expansion of genetically unstable cells. The presence and extent of genomic instability, as measured by mutational load (ML), was examined in a preliminary longitudinal study of BE patients.

Methods: An IRB approved database was used to retrospectively identify two groups of BE patients: non-progressors were defined as patients (N=5) with stable BE over a minimum of 4 years follow up (and 3 biopsies) without the presence of HGD or EA, and progressors were defined as patients (N=6) exhibiting HGD or EA in a final biopsy with less advanced neoplasia in a previous biopsy. The average surveillance time was 6.0 years (median 6.8) for non-progressors and 2.7 years (median 2.4) for progressors. Biopsy slides were microdissected for tissue (targets) containing the most advanced BE neoplasia. DNA from each target (N=60) was tested in a blinded manner for LOH and MSI at 10 genomic loci in proximity to known tumor suppressor genes. The presence and clonality of LOH mutations were combined into an overall measure ML using weightings for low and high clonality and MSI.

Figure 3:
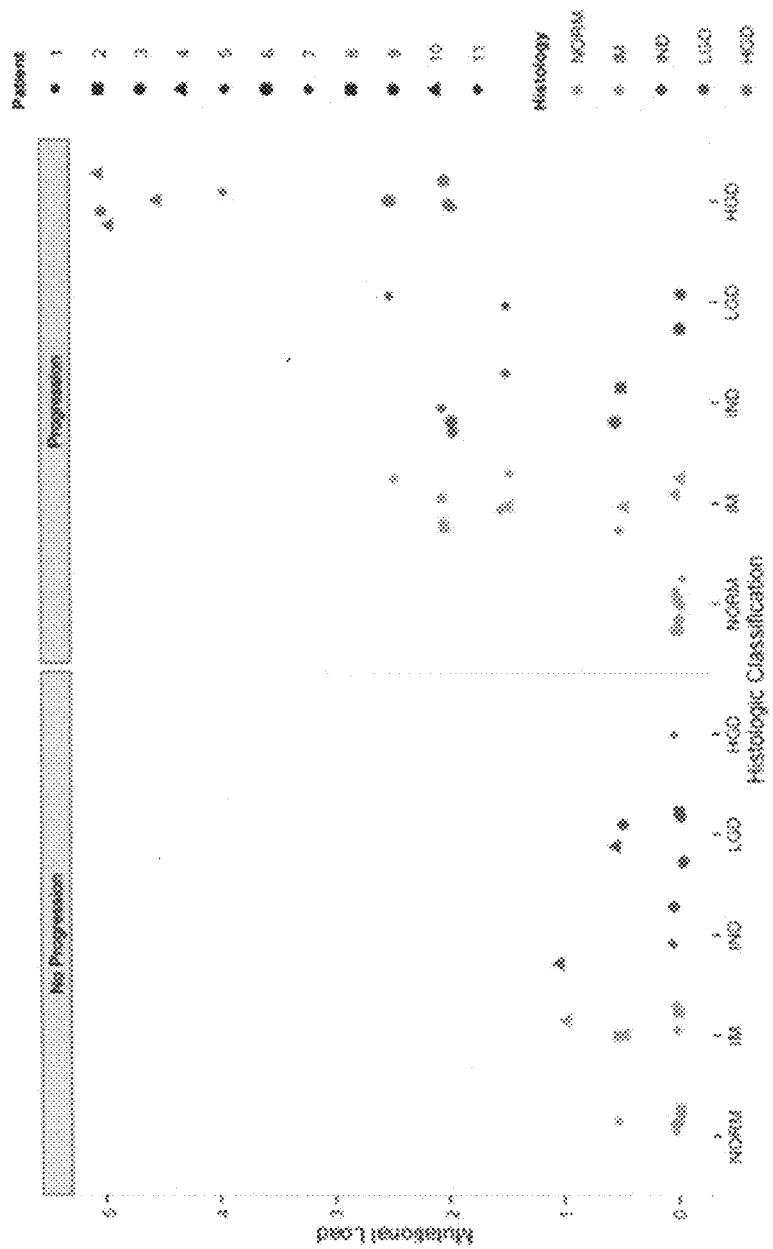
FIG. 3 depicts the correlation of ML with histological classifications of 60 microdissected targets in 6 progressor (38 targets) and 5 non-progressor (22 targets) patients. NORM=normal squamous epithelium; IM=intestinal metaplasia; IND="indefinite for dysplasia"; LGD=low-grade dysplasia; and HGD=high-grade dysplasia.

Results: ML increased with the degree of neoplasia (FIG. 3). The mean ML for non-BE (Norm), intestinal metaplasia (IM), indefinite for dysplasia (IND), low grade dysplasia (LGD), and HGD targets in the progressor and non-progressor groups is listed in Table 11. The progressor group had a higher ML compared to the non-progressor group (average ML 1.6 versus 0.2, respectively, p<0.001). When ML from the final, outcome-determining biopsies was excluded, the average ML in the progressors was 1.1 versus 0.2 in the non-progressors (p=0.003). Importantly, patients from the non-progressors never had an ML greater than 1.

TABLE 11

Average ML in Progressor and Non-progressor histological targets

| | Average ML in histological targets (N) | |
|---|---|---|
| Histology | Non-Progressor | Progressor |
| NORM | 0.1 (6) | 0 (7) |
| IM | 0.3 (6) | 1.3 (11) |
| IND | 0.3 (3) | 1.4 (6) |
| LGD | 0.2 (6) | 1 (4) |
| HGD | 0 (1) | 3.5 (10) |
| All | 0.2 (22) | 1.6 (38) |

Conclusions: ML consistently provides an objective measure of the presence and extent of genomic instability in BE. Subjects with advanced neoplasia have a higher ML than those with less advanced neoplasia. Patients with progressive neoplasia have a greater ML than those without progressive disease. Histology-guided assessment of ML in patients with less advanced BE may provide a more sensitive marker for progressive neoplasia than histology alone.

Example 9

Methods: Specimens were from biopsies of 25 patients with confirmed dysplasia. These specimens were microdissected into 93 distinct microdissection targets, each encompassing a specific area of disease on a specific biopsy slide. Each microdissection target was reviewed by a pathologist blinded to the molecular results and assigned a microscopic diagnosis of normal, intestinal metaplasia, low grade dysplasia, high grade dysplasia or carcinoma.

DNA was extracted from each microdissection target and tested at 22 microsatellites in proximity to 10 known tumor suppressor genes on distinct genomic loci 1p (CMM1, Lmyc), 3p (VHL, OGG1), 5q (MCC, APC), 9p (CDKN2A, CDKN2B), 10q (PTEN, MXI1), 17p (TP53), 17q (NME1), 21q, 22q (NF2). The presence and absence of allelic imbalance mutations, and clonality of mutation were determined for each microsatellite. For each locus, an overall clonality was determined as the maximum clonality observed at any microsatellite marker located near that locus (e.g. 4 markers on 17p). The number of contiguous markers affected by a mutation was also determined for each locus.

Mutational load was calculated for each microdissection target as a weighted count of mutations using weightings as previous described (e.g. 1 for high clonality, 0.5 for low clonality, 0.75 for microsatellite instability (MSI) when it was the only mutation and 1 for MSI together mutations at any other loci).

Figure 4:
FIG. 4 depicts the number of targets with 1, 2, 3, or 4 microsatellite markers affected at particular loci.

Results: Table 12 and FIG. 4 shows the number of targets with 1, 2, 3, or 4 microsatellite markers affected at a particular locus. Mutations encompassing multiple markers at a given locus were only found in targets diagnosed as high grade dysplasia and carcinoma, and were particularly common at 9p and 17p.

Conclusions: Increased length of a mutated segment of the genome appears to be strongly correlated with the presence of high grade dysplasia, and may serve as a marker for progressive disease.

TABLE 12

Length of deleted segment of genome (as measured by number of markers affected at a particular locus), for different histologic grades of disease.

| Histology | # markers affected by mutation | 1p | 3p | 5q | 9p | 10q | 17p | 17q | 18q | 21q | 22q |
|---|---|---|---|---|---|---|---|---|---|---|---|
| Normal Squamous or Gastric Mucosa | 0 | 19 | 19 | 19 | 19 | 19 | 19 | 19 | 19 | 19 | 19 |
|  | 1 | 0 | 0 | 0 | 0 | 0 | 0 | 0 | 0 | 0 | 0 |
|  | 2 | 0 | 0 | 0 | 0 | 0 | 0 | 0 | 0 | 0 | 0 |
|  | 3 | 0 | 0 | 0 | 0 | 0 | 0 | 0 | 0 | 0 | 0 |
|  | 4 | 0 | 0 | 0 | 0 | 0 | 0 | 0 | 0 | 0 | 0 |
| Intestinal Metaplasia | 0 | 7 | 7 | 7 | 7 | 7 | 7 | 7 | 7 | 7 | 7 |
|  | 1 | 0 | 0 | 0 | 0 | 0 | 0 | 0 | 0 | 0 | 0 |
|  | 2 | 0 | 0 | 0 | 0 | 0 | 0 | 0 | 0 | 0 | 0 |
|  | 3 | 0 | 0 | 0 | 0 | 0 | 0 | 0 | 0 | 0 | 0 |
|  | 4 | 0 | 0 | 0 | 0 | 0 | 0 | 0 | 0 | 0 | 0 |
| High Grade Dysplasia | 0 | 25 | 23 | 29 | 9 | 27 | 11 | 27 | 19 | 26 | 30 |
|  | 1 | 9 | 7 | 1 | 7 | 7 | 10 | 7 | 12 | 8 | 4 |
|  | 2 | 0 | 4 | 4 | 6 | 0 | 7 | 0 | 3 | 0 | 0 |
|  | 3 | 0 | 0 | 0 | 10 | 0 | 3 | 0 | 0 | 0 | 0 |
|  | 4 | 0 | 0 | 0 | 3 | 0 | 6 | 0 | 0 | 0 | 0 |
| Carcinoma | 0 | 13 | 11 | 11 | 11 | 18 | 7 | 13 | 6 | 22 | 14 |
|  | 1 | 6 | 6 | 6 | 5 | 7 | 9 | 12 | 10 | 3 | 11 |
|  | 2 | 6 | 8 | 8 | 2 | 0 | 4 | 0 | 9 | 0 | 0 |
|  | 3 | 0 | 0 | 0 | 4 | 0 | 0 | 0 | 0 | 0 | 0 |
|  | 4 | 0 | 0 | 0 | 3 | 0 | 5 | 0 | 0 | 0 | 0 |

Example 10—Calculation of Mutational Load

Table 13 depicts the calculation of mutational load in a series of 20 patients. In some cases, several specimens from a single patient were tested (see Table 13, "Target" column). Mutational load was calculated based on the number of loci with high clonality mutations, the number of low clonality mutations and the number of loci displaying microsatellite instability.

As can be seen in Table 13, mutational load correlates with a more severe diagnosis based on histology.

TABLE 13

Mutational Load calculation

| Patient | Target | Diagnosis based on histology | Number of loci with high clonality mutations | Number of loci with low clonality mutations | Number of loci displaying microsatellite instability | Mutational load |
|---|---|---|---|---|---|---|
| 1 | 1N | Normal Squamous Epithelium | 0 | 0 | 0 | 0 |
| 1 | 2X | High-Grade Dysplasia | 3 | 0.5 | 0 | 3.5 |
| 1 | 3X | High-Grade Dysplasia | 3 | 0.5 | 1 | 4.5 |
| 1 | 4X | High-Grade Dysplasia | 3 | 0.5 | 0 | 3.5 |
| 1 | 5X | High-Grade Dysplasia | 3 | 0.5 | 0 | 3.5 |
| 2 | 1N | Normal Squamous Epithelium | 0 | 0 | 0 | 0 |
| 2 | 2X | High-Grade Dysplasia | 1 | 0.5 | 0 | 1.5 |
| 2 | 3X | Low-Grade Dysplasia | 1 | 1.5 | 0 | 2.5 |
| 2 | 4X | High-Grade Dysplasia | 2 | 0.5 | 0 | 2.5 |
| 2 | 5X | Indefinite for Dysplasia | 0 | 0 | 0 | 0 |
| 2 | 6X | Low-Grade Dysplasia | 1 | 0 | 0 | 1 |
| 3 | 1N | Normal Gastroesophageal Junction | 0 | 0 | 0 | 0 |
| 3 | 2X | Low-Grade Dysplasia | 0 | 0.5 | 2 | 2.5 |
| 3 | 3X | High-Grade Dysplasia | 1 | 1.5 | 1 | 3.5 |
| 4 | 1N | Intestinal Metaplasia | 0 | 0 | 0 | 0 |
| 4 | 2X | Low-Grade Dysplasia | 0 | 0.5 | 0 | 0.5 |
| 4 | 3X | Low-Grade Dysplasia | 0 | 0 | 0.75 | 0.75 |
| 5 | 1N | Normal Squamous Epithelium | 0 | 0 | 0 | 0 |
| 5 | 2X | Indefinite for Dysplasia | 0 | 2 | 0 | 2 |
| 5 | 3X | Low-Grade Dysplasia | 0 | 0.5 | 0 | 0.5 |
| 6 | 1X | Intestinal Metaplasia | 0 | 0 | 0 | 0 |
| 6 | 2X | Low-Grade Dysplasia | 0 | 2 | 0 | 2 |
| 6 | 3X | Low-Grade Dysplasia | 0 | 0.5 | 0 | 0.5 |
| 6 | 4X | Indefinite for Dysplasia | 0 | 1.5 | 1 | 2.5 |
| 6 | 5X | Low-Grade Dysplasia | 0 | 1 | 0 | 1 |
| 7 | 1X | Intestinal Metaplasia | 0 | 0 | 0 | 0 |
| 7 | 2X | Low-Grade Dysplasia | 0 | 0 | 0 | 0 |
| 8 | 3X | Low-Grade Dysplasia | 0 | 0 | 0 | 0 |
| 9 | 1X | High-Grade Dysplasia | 4 | 0 | 1 | 5 |
| 9 | 2X | High-Grade Dysplasia | 0 | 1 | 3 | 4 |

TABLE 13-continued

Mutational Load calculation

| Patient | Target | Diagnosis based on histology | Number of loci with high clonality mutations | Number of loci with low clonality mutations | Number of loci displaying microsatellite instability | Mutational load |
|---|---|---|---|---|---|---|
| 9 | 3X | High-Grade Dysplasia | 4 | 1 | 1 | 6 |
| 9 | 4X | High-Grade Dysplasia | 0 | 1 | 1 | 2 |
| 9 | 5X | High-Grade Dysplasia | 0 | 1 | 1 | 2 |
| 9 | 6X | High-Grade Dysplasia | 2 | 0.5 | 0 | 2.5 |
| 10 | 1N | Normal Squamous Epithelium | 0 | 0 | 0 | 0 |
| 10 | 2X | Intramucosal Carcinoma | 0 | 1 | 0 | 1 |
| 10 | 3X | Intramucosal Carcinoma | 0 | 1.5 | 0 | 1.5 |
| 11 | 1N | Normal Squamous Epithelium | 0 | 0 | 0 | 0 |
| 11 | 2X | Low-Grade Dysplasia | 2 | 1 | 3 | 6 |
| 11 | 3X | Low-Grade Dysplasia | 3 | 1 | 2 | 6 |
| 12 | 1N | Normal Muscularis Propria | 0 | 0 | 0 | 0 |
| 12 | 2X | High-Grade Dysplasia | 2 | 2 | 0 | 4 |
| 12 | 3X | High-Grade Dysplasia | 5 | 1.5 | 0 | 6.5 |
| 13 | 1N | Normal Muscularis Propria | 0 | 0 | 0 | 0 |
| 13 | 2X | Invasive Adenocarcinoma | 5 | 1 | 0 | 6 |
| 13 | 3X | Low-Grade Dysplasia | 0 | 0 | 0 | 0 |
| 14 | 1N | Normal Esophageal Glands | 0 | 0 | 0 | 0 |
| 14 | 2X | Invasive Adenocarcinoma | 2 | 2 | 0 | 4 |
| 15 | 1N | Invasive Adenocarcinoma | 0 | 0 | 0 | 0 |
| 15 | 2T | High-Grade Dysplasia | 1 | 1 | 0 | 2 |
| 16 | 1N | Normal Gastric Mucosa | 0 | 0 | 0 | 0 |
| 16 | 2T | Invasive Adenocarcinoma | 1 | 1.5 | 0 | 2.5 |
| 16 | 3X | Low-Grade Dysplasia | 0 | 0 | 0 | 0 |
| 16 | 4T | Invasive Adenocarcinoma | 0 | 0 | 0 | 0 |
| 17 | 1N | Inflamed Gastric Mucosa (No Dysplasia) | 0 | 0 | 0 | 0 |
| 17 | 2T | Adenocarcinoma | 2 | 0.5 | 0 | 2.5 |
| 18 | 1N | Normal Squamous Epithelium | 0 | 0 | 0 | 0 |
| 18 | 2T | Invasive Adenocarcinoma | 0 | 3 | 0 | 3 |
| 19 | 1N | Normal Gastric Mucosa | 0 | 0 | 0 | 0 |
| 19 | 2T | Invasive Adenocarcinoma | 2 | 3.5 | 0 | 5.5 |
| 19 | 3T | Invasive Adenocarcinoma | 2 | 2 | 1 | 5 |
| 19 | 4T | Invasive Adenocarcinoma | 0 | 4 | 1 | 5 |
| 19 | 5T | Invasive Adenocarcinoma | 0 | 4 | 1 | 5 |
| 20 | 1N | Normal Gastric Mucosa | 0 | 0 | 0 | 0 |
| 20 | 2T | Invasive Adenocarcinoma | 0 | 0 | 0 | 0 |
| 20 | 3T | Invasive Adenocarcinoma | 0 | 1.5 | 3 | 4.5 |

Example 11—Calculation of Mutational Load Based on Differential Weighting of Loci Table 14 shows the calculation of mutational load based on differing weightings being assigned to particular loci in a group of 20 patients. In some cases, several specimens from a single patient were tested (see Table 14, "Target" column). Certain loci were assigned higher weightings based on known associations with disease progression. The mutational loads calculated this was correlated with disease diagnosis based on histology.

TABLE 14

Calculation of mutational load based on differing loci weightings

| Patient | Target | Diagnosis by histology | Mutational Load by loci | | | | | | | | | | Mutational Load |
|---|---|---|---|---|---|---|---|---|---|---|---|---|---|
| | | | 1p | 3p | 5q | 9p | 10q | 17p | 17q | 18q | 21q | 22q | |
| 1 | 1N | Normal Squamous Epithelium | 0 | 0 | 0 | 0 | 0 | 0 | 0 | 0 | 0 | 0 | 0 |
| 1 | 2X | High-Grade Dysplasia | 0 | 0 | 0 | 1.75 | 0 | 1.5 | 0 | 0.5 | 1 | 0 | 3 |
| 1 | 3X | High-Grade Dysplasia | 0 | 0 | 0 | 1.75 | 1 | 1.5 | 0 | 1 | 0.5 | 0 | 4 |
| 1 | 4X | High-Grade Dysplasia | 0 | 0 | 0 | 1.75 | 0 | 1.5 | 0 | 0.5 | 1 | 0 | 3 |
| 1 | 5X | High-Grade Dysplasia | 0 | 0 | 0 | 1.75 | 0 | 1.5 | 0 | 0.5 | 1 | 0 | 3 |
| 2 | 1N | Normal Squamous Epithelium | 0 | 0 | 0 | 0 | 0 | 0 | 0 | 0 | 0 | 0 | 0 |
| 2 | 2X | High-Grade Dysplasia | 0.5 | 0 | 0 | 0 | 0 | 2 | 0 | 0 | 0 | 0 | 2 |

TABLE 14-continued

Calculation of mutational load based on differing loci weightings

| Patient | Target | Diagnosis by histology | Mutational Load by loci | | | | | | | | | | Mutational Load |
|---|---|---|---|---|---|---|---|---|---|---|---|---|---|
| | | | 1p | 3p | 5q | 9p | 10q | 17p | 17q | 18q | 21q | 22q | |
| 2 | 3X | Low-Grade Dysplasia | 0.5 | 0 | 0 | 0.75 | 0 | 2 | 0 | 0 | 0 | 0.5 | 2.5 |
| 2 | 4X | High-Grade Dysplasia | 0 | 1 | 0 | 2 | 0 | 1.5 | 0 | 0 | 0 | 0 | 1.5 |
| 2 | 5X | Indefinite for Dysplasia | 0 | 0 | 0 | 0 | 0 | 0 | 0 | 0 | 0 | 0 | 0 |
| 2 | 6X | Low-Grade Dysplasia | 0 | 0 | 0 | 0 | 0 | 1.5 | 0 | 0 | 0 | 0 | 1.5 |
| 3 | 1N | Normal Gastroesophageal Junction | 0 | 0 | 0 | 0 | 0 | 0 | 0 | 0 | 0 | 0 | 0 |
| 3 | 2X | Low-Grade Dysplasia | 0 | 0 | 0 | 1 | 0 | 1.5 | 0 | 1 | 0 | 0 | 2.5 |
| 3 | 3X | High-Grade Dysplasia | 0 | 0.5 | 0 | 1 | 0.5 | 2 | 0 | 0 | 0 | 0.5 | 3 |
| 4 | 1N | Intestinal Metaplasia | 0 | 0 | 0 | 0 | 0 | 0 | 0 | 0 | 0 | 0 | 0 |
| 4 | 2X | Low-Grade Dysplasia | 0 | 0 | 0 | 1.5 | 0 | 0 | 0 | 0 | 0 | 0 | 0 |
| 4 | 3X | Low-Grade Dysplasia | 0 | 0 | 0 | 0 | 0 | 0 | 1 | 0 | 0 | 0 | 1 |
| 5 | 1N | Normal Squamous Epithelium | 0 | 0 | 0 | 0 | 0 | 0 | 0 | 0 | 0 | 0 | 0 |
| 5 | 2X | Indefinite for Dysplasia | 0 | 0.5 | 0 | 1.5 | 0 | 1.25 | 0.5 | 0 | 0 | 0 | 1.75 |
| 5 | 3X | Low-Grade Dysplasia | 0 | 0 | 0 | 1 | 0 | 0 | 0 | 0 | 0 | 0 | 0 |
| 6 | 1X | Intestinal Metaplasia | 0 | 0 | 0 | 0 | 0 | 0 | 0 | 0 | 0 | 0 | 0 |
| 6 | 2X | Low-Grade Dysplasia | 0.5 | 0 | 0 | 1 | 0 | 0.75 | 0.5 | 0 | 0 | 0 | 1.25 |
| 6 | 3X | Low-Grade Dysplasia | 0 | 0 | 0 | 1 | 0 | 0 | 0 | 0 | 0 | 0 | 0 |
| 6 | 4X | Indefinite for Dysplasia | 0.5 | 1 | 0 | 1 | 0 | 0 | 0.5 | 0 | 0 | 0 | 0.5 |
| 6 | 5X | Low-Grade Dysplasia | 0 | 0 | 0 | 1 | 0 | 0 | 0.5 | 0 | 0 | 0 | 0.5 |
| 7 | 1X | Intestinal Metaplasia | 0 | 0 | 0 | 0 | 0 | 0 | 0 | 0 | 0 | 0 | 0 |
| 7 | 2X | Low-Grade Dysplasia | 0 | 0 | 0 | 0 | 0 | 0 | 0 | 0 | 0 | 0 | 0 |
| 8 | 3X | Low-Grade Dysplasia | 0 | 0 | 0 | 0 | 0 | 0 | 0 | 0 | 0 | 0 | 0 |
| 9 | 1X | High-Grade Dysplasia | 1 | 1.25 | 0 | 1.75 | 0 | 0 | 1 | 1.25 | 0 | 0 | 2.25 |
| 9 | 2X | High-Grade Dysplasia | 0.5 | 1 | 0 | 1 | 0 | 0 | 1 | 0.5 | 0 | 0 | 1.5 |
| 9 | 3X | High-Grade Dysplasia | 1 | 1 | 0 | 1.5 | 0.5 | 0.75 | 1 | 1.25 | 0 | 0 | 3.5 |
| 9 | 4X | High-Grade Dysplasia | 0 | 0 | 0 | 1 | 0 | 0.75 | 0 | 0.5 | 0 | 0 | 1.25 |
| 9 | 5X | High-Grade Dysplasia | 0 | 0 | 0 | 1 | 0 | 0.75 | 0 | 0.75 | 0 | 0 | 1.5 |
| 9 | 6X | High-Grade Dysplasia | 0.5 | 0 | 0 | 1.75 | 0 | 1.25 | 0 | 0 | 0 | 0 | 1.25 |
| 10 | 1N | Normal Squamous Epithelium | 0 | 0 | 0 | 0 | 0 | 0 | 0 | 0 | 0 | 0 | 0 |
| 10 | 2X | Intramucosal Carcinoma | 0 | 0.5 | 0 | 1 | 0 | 0 | 0 | 0 | 0 | 0 | 0 |
| 10 | 3X | Intramucosal Carcinoma | 0 | 0.5 | 0 | 1.25 | 0 | 0 | 0 | 0.5 | 0 | 0 | 0.5 |
| 11 | 1N | Normal Squamous Epithelium | 0 | 0 | 0 | 0 | 0 | 0 | 0 | 0 | 0 | 0 | 0 |
| 11 | 2X | Low-Grade Dysplasia | 0 | 1 | 1 | 0 | 1 | 1.75 | 1 | 0.5 | 0.5 | 0 | 4.75 |
| 11 | 3X | Low-Grade Dysplasia | 0 | 1 | 1.25 | 0 | 0.5 | 1.75 | 1 | 0.5 | 1 | 0 | 4.75 |
| 12 | 1N | Normal Muscularis Propria | 0 | 0 | 0 | 0 | 0 | 0 | 0 | 0 | 0 | 0 | 0 |
| 12 | 2X | High-Grade Dysplasia | 0 | 0.75 | 1.25 | 0.75 | 0.5 | 1.5 | 0 | 0 | 0 | 0.5 | 2.5 |
| 12 | 3X | High-Grade Dysplasia | 0 | 0.5 | 1.25 | 1.25 | 1 | 1.5 | 0 | 0.5 | 0.5 | 1 | 4.5 |

TABLE 14-continued

Calculation of mutational load based on differing loci weightings

| Patient | Target | Diagnosis by histology | Mutational Load by loci | | | | | | | | | | Mutational Load |
|---|---|---|---|---|---|---|---|---|---|---|---|---|---|
| | | | 1p | 3p | 5q | 9p | 10q | 17p | 17q | 18q | 21q | 22q | |
| 13 | 1N | Normal Muscularis Propria | 0 | 0 | 0 | 0 | 0 | 0 | 0 | 0 | 0 | 0 | 0 |
| 13 | 2X | Invasive Adenocarcinoma | 1.25 | 1.25 | 1 | 1.25 | 0.5 | 0.75 | 0 | 1 | 0 | 0 | 2.25 |
| 13 | 3X | Low-Grade Dysplasia | 0 | 0 | 0 | 0 | 0 | 0 | 0 | 0 | 0 | 0 | 0 |
| 14 | 1N | Normal Esophageal Glands | 0 | 0 | 0 | 0 | 0 | 0 | 0 | 0 | 0 | 0 | 0 |
| 14 | 2X | Invasive Adenocarcinoma | 0 | 0 | 0.5 | 1.75 | 0.5 | 1.25 | 0.5 | 0.5 | 0 | 0 | 2.75 |
| 15 | 1N | Invasive Adenocarcinoma | 0 | 0 | 0 | 0 | 0 | 0 | 0 | 0 | 0 | 0 | 0 |
| 15 | 2T | High-Grade Dysplasia | 0 | 0 | 0 | 0.75 | 0 | 0.75 | 1 | 0 | 0 | 0 | 1.75 |
| 16 | 1N | Normal Gastric Mucosa | 0 | 0 | 0 | 0 | 0 | 0 | 0 | 0 | 0 | 0 | 0 |
| 16 | 2T | Invasive Adenocarcinoma | 0 | 0.5 | 0.5 | 0 | 0 | 1.25 | 0 | 0.5 | 0 | 0 | 1.75 |
| 16 | 3X | Low-Grade Dysplasia | 0 | 0 | 0 | 0 | 0 | 0 | 0 | 0 | 0 | 0 | 0 |
| 16 | 4T | Invasive Adenocarcinoma | 0 | 0 | 0 | 0 | 0 | 0 | 0 | 0 | 0 | 0 | 0 |
| 17 | 1N | Inflamed Gastric Mucosa (No Dysplasia) | 0 | 0 | 0 | 0 | 0 | 0 | 0 | 0 | 0 | 0 | 0 |
| 17 | 2T | Adenocarcinoma | 0 | 0 | 0 | 1.25 | 0 | 0.75 | 0 | 1.25 | 0 | 0 | 2 |
| 18 | 1N | Normal Squamous Epithelium | 0 | 0 | 0 | 0 | 0 | 0 | 0 | 0 | 0 | 0 | 0 |
| 18 | 2T | Invasive Adenocarcinoma | 0.5 | 0.5 | 0 | 0.75 | 0 | 1 | 0.5 | 0.75 | 0 | 0 | 2.25 |
| 19 | 1N | Normal Gastric Mucosa | 0 | 0 | 0 | 0 | 0 | 0 | 0 | 0 | 0 | 0 | 0 |
| 19 | 2T | Invasive Adenocarcinoma | 0.75 | 1.25 | 0.75 | 2 | 0.5 | 1 | 0.5 | 0.75 | 0 | 0.5 | 3.25 |
| 19 | 3T | Invasive Adenocarcinoma | 1.25 | 1 | 1.25 | 0.75 | 0.5 | 0 | 0 | 0.5 | 0 | 0.5 | 1.5 |
| 19 | 4T | Invasive Adenocarcinoma | 0.75 | 1 | 0.75 | 1.5 | 0.5 | 0.75 | 0.5 | 0.75 | 0 | 0.5 | 3 |
| 19 | 5T | Invasive Adenocarcinoma | 0.75 | 1 | 0.75 | 1.5 | 0.5 | 1 | 0.5 | 0.75 | 0 | 0.5 | 3.25 |
| 20 | 1N | Normal Gastric Mucosa | 0 | 0 | 0 | 0 | 0 | 0 | 0 | 0 | 0 | 0 | 0 |
| 20 | 2T | Invasive Adenocarcinoma | 0 | 0 | 0 | 0 | 0 | 0 | 0 | 0 | 0 | 0 | 0 |
| 20 | 3T | Invasive Adenocarcinoma | 0 | 0.5 | 1 | 1 | 0 | 0 | 0.5 | 1 | 0 | 1 | 2.5 |

Example 12—Assessment of Mutational Load in Biopsy Tissue Provides Additional Information about Genomic Instability to Histological Classifications of Barrett's Esophagus Abstract Goals: We examined the presence and extent of genomic instability in advanced and less advanced Barrett's Esophagus (BE) histology using mutational load (ML).

Background: Progression of BE to esophageal adenocarcinoma (EAC) is associated with accumulated genomic instability. Current risk stratification of BE for EAC relies on histological classification and grade of dysplasia. However, histology alone cannot assess the risk of patients with inconsistent or non-dysplastic BE histology.

Study: We therefore examined genomic instability of advanced and less advanced BE histology using ML. ML summarized the presence and clonality of loss of heterozygosity (LOH) mutations and the emergence of new alleles, manifested as microsatellite instability (MSI) mutations, in 10 genomic loci around tumor suppressor genes associated with EAC. The ML of 877 microdissected targets from BE biopsies was correlated to their histology. Histological targets were categorized into three levels: no ML, low ML, and high ML.

Results: Increasing ML correlated with increasingly severe histology. A portion of targets with non-dysplastic and low-grade histology shared a similar ML as those with higher risk and EAC disease. By contrast, proportions of targets that lacked mutations decreased with increasingly severe histology. The addition of MSI characterization to ML helped to differentiate the ML between advanced and less advanced histology.

Conclusions: Given that EAC is associated with accumulated genomic instability, high ML in less severe histology may identify BE disease at greater risk of progression to EAC. ML may help to better manage BE in early histological stages and when histology alone provides insufficient information.

Introduction

Esophageal adenocarcinoma (EAC) exhibits the highest rate of increasing incidence of any solid cancer in the U.S.

today, and Barrett's esophagus (BE) represents a precursor of and largest risk factor for EAC. The carcinogenesis of BE has been associated with morphologic changes in esophageal tissue as well as activation of oncogenes and inactivation of tumor suppressor genes. Studies have shown that variable degrees of mutational change take place in the microsatellite regions of tumor suppressor genes at the histological onset of BE. The cumulative buildup of various mutations has been closely associated with the different histological grades of BE and EAC. Histological progression to EAC is associated with a relatively poor prognosis, with a 5-year survival rate for regional cancer below 18%. Consequently, emphasis has been placed upon understanding the risk for progression to EAC of each histological stage of BE such that patients can be appropriately managed with intervention or surveillance.

Accurate histological classification is essential for properly detecting BE at its earliest stages. Guidelines currently define BE as specialized intestinal metaplasia with goblet cells and grade BE samples with the following progressive histological classifications: intestinal metaplasia (IM), indefinite for dysplasia (IND), low-grade dysplasia (LGD), and high-grade dysplasia (HGD). The most advanced, HGD, has been associated with a greater risk of progression to EAC.

Both BE and EAC can be readily identified by microscopic examination, but the presence and different grades of dysplasia can be difficult to diagnose due to challenges in discriminating reactive epithelial atypia from true dysplasia. The classification of indefinite for dysplasia is sometimes provided when cellular atypia is observed, but the criteria for the histological diagnosis of dysplasia are not fully met. Poor orientation of the histological sections and presence of inflammatory infiltrate are among the most common factors interfering with the pathologist's ability to differentiate between the presence or absence of dysplasia. Inter-observer variability in the histological classification of BE has been reported by various studies. Most variability is linked to LGD, yet some variability is also seen in cases of HGD, complicating the decision as to how to clinically manage patients.

Non-dysplastic histological features are limited when it comes to determining whether or not a case of BE is likely to progress to cancer or remain stable, as there are no observable non-dysplastic histological microscopic features that can reveal a patient's likelihood of cancer progression. Because of this uncertainty, many choose ablation interventions for low grade dysplastic and non-dysplastic BE, which has provoked concerns about unnecessary healthcare expenditures. Supplementary diagnostic information that enables better characterization of the risk for less advanced stages of BE disease would be valuable in improving patient care and controlling healthcare costs.

Herein, we aimed to provide additional information to the histological classification of less advanced stages of BE by showing the relationship between BE histology and the presence and extent of genomic instability in multiple study cohorts. Previous investigation has shown that three or more DNA abnormalities in less advanced stages of BE are associated with a higher risk of cancer progression. Two of these abnormalities were loss of heterozygosity (LOH) mutations in microsatellite regions of the TP53 and CDKN2A tumor suppressor genes. Increasing sizes of genetically instable clones with TP53 and CDKN2A LOH have also been associated with increased risk of progression to EAC.

We therefore studied the presence and extent (clonality) of genomic instability in advanced and less advanced BE histology in a cross-sectional study of patients from multiple study cohorts. Genomic instability was assessed by mutational load in histological targets microdissected from BE patient biopsy tissue. Mutational load summarized the presence and extent of LOH next to TP53 and CDKN2A as well as LOH in 8 additional genomic loci next to tumor suppressor genes. Microsatellite instability (MSI) around these tumor suppressor genes was also included in the assessment of mutational load. Our results demonstrate that histology-guided assessment for mutational load provides an objective measure of the presence and extent of genomic instability. Assessment for mutational load provides an added dimension to less advanced BE histology that could help to better manage BE patients in early or uncertain histological stages of disease.

Materials and Methods

Study Cohort: Standard histological sections (4 µm thick) of formalin-fixed, paraffin-embedded (FFPE) tissue were examined from 415 patients histologically known to have BE. Microdissection of 661 biopsy slides yielded 877 targets in total from three study sites, each with IRB approval of their corresponding study protocol (IRB#26163, IRB #11-29, IRB #5658 and IRB#5629). All patients in the study had previously undergone upper GI endoscopy. Patients without evidence of BE were excluded.

Histological Classification: Hematoxylin and eosin (H&E) stained, FFPE histology slides underwent microscopic evaluation for the selection of targets for subsequent microdissection. Each target was histologically classified as follows: normal squamous epithelium, columnar mucosa (COL), and, in order of increasing severity: intestinal metaplasia (IM), indefinite for dysplasia (IND), low grade dysplasia (LGD), high grade dysplasia (HGD), and esophageal adenocarcinoma (EAC). BE histological classification began with intestinal metaplasia histology. A histological classification was assigned based on pathologist review of tissue. All pathologists were blinded to molecular results. In one study cohort from Norwalk Hospital, three pathologists classified the same microdissected targets. Consensus diagnosis was defined as agreement between at least two pathologists.

Microdissection: Hematoxylin and eosin (H&E) stained, FFPE slides were used as guides to microdissect tissue (targets) with BE histology from 1-3 unstained, serial FFPE slides of each patient. Microdissected targets corresponded to distinct foci of tissue with EAC histology, BE histology, columnar mucosa histology, or normal epithelial histology, as identified by a pathologist. Normal epithelial and columnar mucosa (COL) targets were microdissected from the same FFPE slides as targets with various histological classifications of BE or EAC histology. Microscopic review confirmed the accuracy of all microdissections.

Detection of LOH and MSI: Detection of LOH and new alleles consistent with microsatellite instability (MSI) were investigated at 10 individual genomic loci, using a panel of 22 DNA markers associated with common tumor suppressor genes relevant to BE. The presence of MSI at BAT25 and BAT26 loci were also examined in a subset of microdissected targets. LOH and MSI were assessed using PCR and quantitative capillary electrophoresis of DNA extracted from each microdissected target, as previous described. DNA markers for the following chromosomal loci comprised the panel (associated genes in parentheses): 1p (CMM1, L-myc), 3p (VHL, HoGG1), 5q (MCC, APC), 9p (CDKN2A), 10q (PTEN, MXI1), 17p (TP53), 17q (NME1), 18q (DCC), 21q (TFF1 and PSEN2) and 22q (NF2).

Quantitative PCR (qPCR) for housekeeping genes was used to ensure there was sufficient, high quality DNA available for analysis prior to LOH and MSI analysis. The analyses were performed on both BE microdissection samples as well as internal controls (normal appearing squamous and columnar mucosa), which were all subject to equivalent formalin fixation and histological processing. PCR amplification and subsequent mutational analysis using quantitative capillary electrophoresis methods were then performed on all microdissected samples with adequate qPCR results.

To determine if each LOH analysis was assessable in each patient, the informativeness (heterozygosity) of each LOH marker in normal epithelial from each patient was first examined by quantitative capillary electrophoresis methods. Normal epithelial targets were also used to account for minor differences in the amplification rates of the two allele lengths during PCR. PCR amplification and subsequent quantitative capillary electrophoresis of DNA from each microdissected target was then performed to assess LOH and MSI.

LOH was called "present" in microdissected targets when there was a degree of allelic imbalance that was equal to or beyond two standard deviations above the average difference in allele peak heights for DNA in normal epithelial microdissection targets. The extent (clonality) of LOH was determined using the ratio of allele peak heights in DNA from microdissected targets, which is proportional to the amount of LOH mutated DNA present in the sample. All DNA specimens with LOH were tested in duplicate or triplicate to ensure reproducibility. LOH mutations were considered high clonality when >75% of the DNA had LOH mutation and low clonality when 50-75% of the DNA had LOH mutation.

MSI was defined by the presence of additional minor, but reproducible, peaks in the electropherograms after PCR amplification and subsequent quantitative capillary electrophoresis of DNA from each target. The minor peaks did not correspond to either of the two major allele lengths present in normal epithelial control DNA and were not accountable by the presence of shadow band formation during capillary gel electrophoresis. The minor peaks were reproducible through replicate confirmatory PCR amplification and further quantitative capillary electrophoresis testing.

Mutational Load: Mutational load measured the presence and clonality of LOH mutations and the presence of MSI at each genomic locus examined. The presence and clonality of LOH mutation at each genomic locus was determined for each microdissected target. Low clonality LOH was defined as 50-75% of the DNA containing LOH, and high clonality LOH was defined as >75% of the DNA containing LOH. All LOH mutations at a given genomic loci were assigned a numerical value based on their low or high clonality. A proportional value of 0.5 was assigned for low clonality mutations and 1 for high clonality mutations using proportional odds logistic regression (POLR), as previously described. The presence of MSI was also assigned a proportional value using POLR. The proportional value of MSI present at a single genomic locus was 0.75. The proportional value of each additional MSI present, beyond one locus, was 0.5. These numerical values for low clonality and high clonality LOH mutations (FIG. 5A) as well as MSI mutations (FIG. 5B) were added together for all loci containing LOH and/or MSI in a microdissected target. The resulting cumulative value was defined as the mutation load (ML) for that microdissected target.

Polyserial correlation coefficient was used to examine the correlation between histological class and mutational load of microdissected targets when mutational load was assessed using only LOH mutations (FIG. 5A) or both LOH and MSI mutations (FIG. 5B). An analysis of variance (ANOVA) model was used to examine the difference in mutational load between advanced (HGD, EAC) and less advanced (IM, IND, LGD) histological classifications when mutational load included only LOH analysis as compared to when it included both LOH and MSI analysis. ANOVA was performed with an interaction term between the two methods of mutational load assessment (LOH only, LOH and MSI) and the two categories of histological classifications of BE (advanced histology, less advanced histology).

Three levels of mutational load (ML) were defined using the distribution of mutational load present in the population of targets with intestinal metaplasia histology. 1) "No ML" contained microdissected targets that lacked mutations. 2) "Low ML" contained targets that had mutations and therefore had ML, but the level of ML in this category was below the top fifth percentile of intestinal metaplasia targets that had the highest ML. 3) "High" ML contained microdissected targets with a mutational load similar to those targets in the top fifth percentile of intestinal metaplasia targets with the highest mutational load. These levels of ML were applied to all histological classifications.

Results

The presence of LOH and MSI in histological classifications: Mutational analysis was performed on 877 microdissected targets corresponding to 661 esophageal biopsy slides from 415 patients. The average number of low clonality and high clonality LOH mutations and MSI mutations in microdissected targets generally increased with increasingly severe histology (Table 15). MSI mutations occurred less often than LOH mutations, but generally increased with increasingly severe histological classifications. LOH mutations were also most abundant in targets with dysplastic histology and occurred on average more often than MSI in HGD and EAC. Low clonality LOH and MSI mutations were detected in similar or higher abundance than high clonality LOH mutations in less severe histological classifications (IM, IND, LGD), suggesting these mutations may occur prior to the appearance of more advanced histological stages of BE.

TABLE 15

Average number of mutations detected in microdissected targets with each histology (COL = columnar mucosa; IM = intestinal metaplasia; IND = "indefinite for dysplasia"; LGD = low grade dysplasia; HGD = high grade dysplasia; EAC = esophageal adenocarcinoma).

| Histological Classification | Total Micro. Targets Tested | Average number of mutated loci detected per micro. target | Average number of Low/High Clonality LOH and MSI mutations detected micro. target | | | Average Mutational Load (ML) |
|---|---|---|---|---|---|---|
| | | | Low | High | MSI | |
| COL | 99 | 0.5 | 0.5 | 0.0 | 0.0 | 0.3 |
| IM | 427 | 1.1 | 0.7 | 0.1 | 0.3 | 0.7 |
| IND | 182 | 1.9 | 1.4 | 0.3 | 0.2 | 1.1 |
| LGD | 85 | 2.7 | 1.7 | 0.6 | 0.5 | 1.8 |
| HGD | 61 | 4.3 | 2.2 | 1.6 | 0.8 | 3.2 |
| EAC | 23 | 5.9 | 4.3 | 1.3 | 0.8 | 3.9 |

Mutations were observed across the entire panel of genomic loci examined. Table 16 describes the percentages of microdissected targets mutated at each of the 10 genomic loci for each histological classification. The percentages of LOH and MSI mutated targets generally increased with more advanced histological classifications, from columnar mucosa (COL) to HGD. Importantly, LOH and MSI mutations at all loci were detected with less advanced stages of BE histology (IM, IND, LGD) but were found more frequently with more advanced stages of BE histology (HGD, EAC). In less advanced BE histology (IM, IND), the most frequently LOH mutated loci included 9p (CDKN2A), 10q (PTEN, MXI1), and 17p (TP53), 17q (NME1), which is consistent with previous studies. MSI mutations at nearly all loci occurred at a similar frequency in less advanced stages of BE histology. In targets with columnar mucosa (COL), limited MSI and LOH mutations were observed across the panel of loci examined.

TABLE 17

Frequency of pathologist agreement on histological classification in one study cohort.

| | % All Pathologists agree | % One Pathologist disagrees | % All Pathologists disagree |
|---|---|---|---|
| IM (N = 115) | 69 | 30 | 1 |
| IND (N = 19) | 0 | 63 | 37 |
| LGD (N = 8) | 13 | 88 | 0 |
| HGD (N = 4) | 50 | 50 | 0 |

IM = intestinal metaplasia; IND = indefinite for dysplasia; LGD = low-grade dysplasia; HGD = high-grade dysplasia

TABLE 16

The percent microdissected targets with mutations each at each genomic loci by histological classification (COL = columnar mucosa; IM = intestinal metaplasia; IND = "indefinite for dysplasia"; LGD = low grade dysplasia; HGD = high grade dysplasia; EAC = esophageal adenocarcinoma; (—) = 0% targets mutated).

| | | | The percent of microdissected targets with LOH and MSI mutations at each loci in each Histological Classification | | | | | |
|---|---|---|---|---|---|---|---|---|
| Mutation | Loci | Tumor suppressor genes | % COL N = 99 | % IM N = 427 | % IND N = 182 | % LGD N = 85 | % HGD N = 61 | % EAC N = 23 |
| MSI | 1p | CMM1, LMYC | 1 | — | 2 | 1 | 7 | 9 |
| | 3p | VHL, OGG1 | — | 7 | 3 | 11 | 13 | 3 |
| | 5q | MCC, APC | — | 3 | 3 | 7 | — | 4 |
| | 9p | CDKN2A | 2 | 2 | — | 1 | 13 | — |
| | 10q | PTEN, MXI1 | — | 1 | 3 | 2 | 10 | 9 |
| | 17p | TP53 | — | 4 | 2 | 7 | 7 | 9 |
| | 17q | NME1 | — | 2 | 3 | 14 | 11 | 4 |
| | 18q | DCC | — | 5 | 1 | 1 | 10 | 4 |
| | 21q | TFF1, PSEN2 | — | 3 | — | 1 | — | — |
| | 22q | NF2 | — | 2 | — | 4 | 5 | 4 |
| LOH | 1p | CMM1, LMYC | 1 | 5 | 14 | 19 | 34 | 43 |
| | 3p | VHL, OGG1 | 2 | 5 | 18 | 27 | 41 | 61 |
| | 5q | MCC, APC | 11 | 8 | 18 | 20 | 34 | 61 |
| | 9p | CDKN2A | 7 | 32 | 36 | 45 | 72 | 61 |
| | 10q | PTEN, MXI1 | 10 | 7 | 22 | 8 | 15 | 43 |
| | 17p | TP53 | 11 | 11 | 29 | 49 | 87 | 83 |
| | 17q | NME1 | 2 | 7 | 22 | 26 | 21 | 65 |
| | 18q | DCC | — | 1 | 1 | 11 | 38 | 78 |
| | 21q | TFF1, PSEN2 | 5 | 5 | 12 | 24 | 21 | 13 |
| | 22q | NF2 | — | 2 | 1 | 5 | 15 | 48 |

Pathologist Variability amongst Histological Classifications: To understand which histology was most reliably classified for each microdissected target, the agreement amongst three pathologists was examined in one study cohort (Table 17). Consistent with previous reports, most disagreement was linked to indefinite for dysplasia and LGD histology, where in the majority of microdissected targets at least one pathologist disagreed with another (100% IND and 88% LGD). By contrast, all three pathologists agreed on the histological classification of intestinal metaplasia in the majority of microdissected targets (69%). In 50% of microdissected targets all pathologists agreed in classifying HGD, while in the other 50% of targets one disagreed, consistent with previously published studies describing variability amongst HGD calls.

Figure 5:
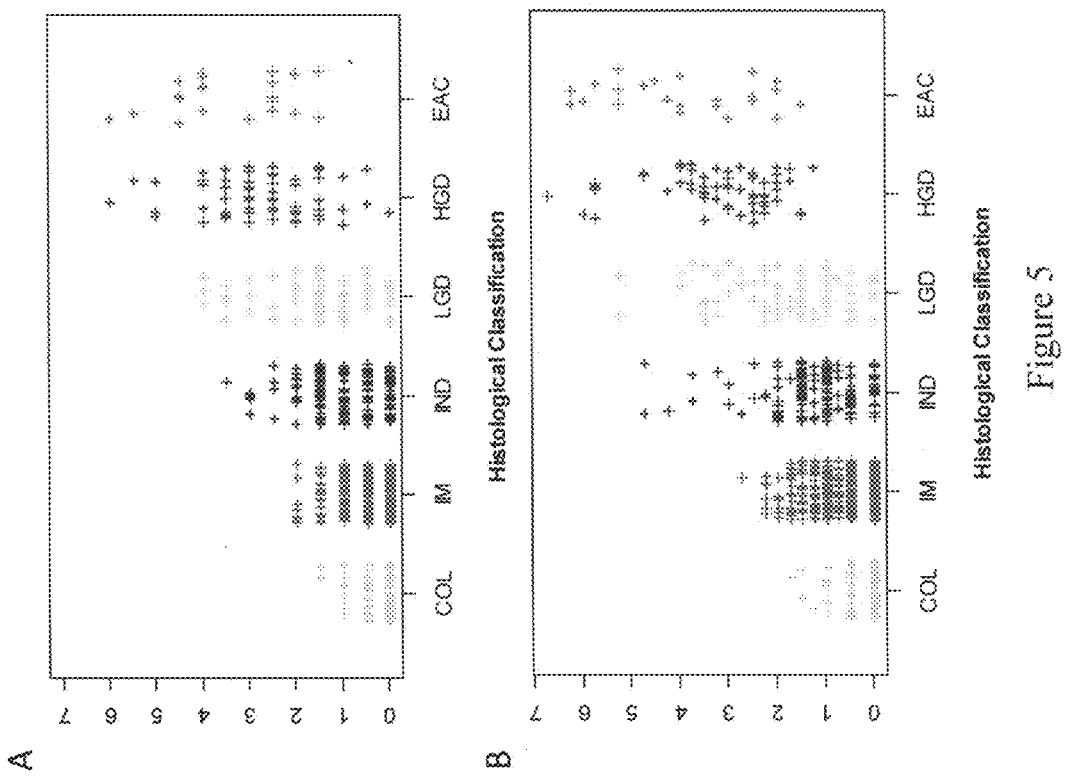
FIG. 5 shows the Correlation of mutational load (ML) to histological classification of microdissected targets A) based on the presence and extent of low and high clonality LOH mutations only (correlation coefficient=0.68, p<0.0001) and B) based on the presence and extent of low and high clonality LOH mutations as well as MSI (correlation coefficient=0.69, p<0.0001). COL=columnar mucosa; IM=intestinal metaplasia; IND="indefinite for dysplasia"; LGD=low-grade dysplasia; HGD=high-grade dysplasia; EAC=esophageal adenocarcinoma.

Assessment of Genomic Instability: The presence and extent (clonality) of genomic instability in each microdissected target was assessed by mutational load. Mutational load of a target was calculated based on the presence and clonality of LOH mutations as well as the presence of MSI in DNA from each histological target. In this system, numerical values were determined by POLR as follows: 0.5 for low clonality LOH mutations (50-75% of DNA had LOH), 0.75 for the first MSI, 0.5 for each additional MSI, and 1 for high clonality LOH mutations (>75% of DNA had LOH). These numerical values for low clonality LOH, MSI, and high clonality LOH mutations were added together for all loci in a microdissected target. The resulting cumulative value was defined as the mutation load for that microdissected target. Consistent with a recent publication in a smaller dataset, the ML of microdissected targets positively correlated with increasingly severe histology (FIG. 5). However, ML in this past publication was only assessed using the presence of low and high clonality LOH mutations. The correlation of increasingly severe histology to ML based on the presence of low and high clonality mutations alone is shown in FIG. 5A (correlation coefficient=0.68, p<0.0001). When a weighted value for MSI mutations was included in the assessment of mutational load (FIG. 1B), the positive correlation between ML and increasingly severe histology was slightly improved (correlation coefficient=0.69, p<0.0001). Importantly, the addition of MSI to the assessment of ML helped to better discriminate the difference in ML between less advanced (IM, IND, LGD) and more advanced (HGD, EAC) histological classifications of BE (FIG. 5A vs. 5B). The average difference in ML between less advanced histology (IM, IND, LGD) and more advance histology (HGD, EAC) was statistically higher when both LOH and MSI was considered as compared to only LOH (2.54 vs. 2.21, p=0.02).

Using the distribution of mutational load present in the population of targets with intestinal metaplasia histology, three levels of mutational load (ML) were established with respect to histological classifications when both LOH and MSI were included in the assessment of mutational load (Table 18). The first level contained microdissected targets that lacked mutations and, as such, had no ML. The second level (low ML) contained targets with a mutational load found in the majority of intestinal metaplasia microdissected targets. Low ML targets had mutations but were below the top fifth percentile of intestinal metaplasia targets with the highest ML. The third level contained microdissected targets with a mutational load similar to those targets in the top fifth percentile of intestinal metaplasia targets with the highest mutational load.

TABLE 18

Percentage (N) of targets with each Mutational Load (ML) by histological classification (COL = columnar mucosa; IM = intestinal metaplasia; IND = indefinite for dysplasia; LGD = low-grade dysplasia; HGD = high-grade dysplasia; EAC = esophageal adenocarcinoma).

| Histology of Microdissected Targets | Mutational Load (ML) | | |
|---|---|---|---|
| | % No ML | % Low ML | % High ML |
| COL (N = 99) | 61 | 38 | 1 |
| IM (N = 427) | 30 | 62 | 8 |
| IND (N = 182) | 18 | 66 | 16 |
| LGD (N = 85) | 8 | 46 | 46 |
| HGD (N = 61) | 0 | 5 | 95 |
| EAC (N = 23) | 0 | 4 | 96 |

Table 18 summarizes the proportion of microdissected targets for each level of mutational load in each histological class. The majority of microdissected histological targets composed of columnar mucosa (COL) had no detectable ML (Table 4). Of the proportion of non-BE targets (COL) that had mutations, all but one were low ML. Of the indefinite for dysplasia microdissected targets 18% had no ML; while the remaining proportion of indefinite for dysplasia targets had mutations, including 66% that had low ML and 16% that had high ML. Most microdissected targets histologically classified as LGD had mutations with the majority of targets falling into the low ML (46%) or high ML (46%) levels. Nearly all HGD (95%) and EAC (96%) histological targets had high ML. Comparatively, only 8% of intestinal metaplasia and 16% of indefinite for dysplasia microdissected targets were characterized as having a high ML.

Discussion

Current risk stratification of BE patients for EAC relies on histological classification and grade of dysplasia. However, histological classification alone cannot sufficiently assess the risk of patients with variable or non-dysplastic BE histology. Progression of BE patients to EAC is associated with accumulated genomic instability. We therefore examined differences in the presence and extent of genomic instability in advanced and less advanced stages of BE histology. Genomic instability was assessed by mutational load, accounting for the presence and clonality of LOH as well as the presence of MSI in 10 genomic loci around tumor suppressor genes associated with EAC (Table 5, Table 16). Our results demonstrate that histology-guided assessment for mutational load provided an objective measure of genomic instability amongst BE histological classifications.

Consistent with previous work, increasing ML correlated with increasingly severe BE histology (Table 15, FIG. 5). The addition of MSI characterization at each of the 10 genomic loci to the assessment of ML slightly increased this correlation (FIGS. 5A and 5B). Studies have published conflicting results regarding the association of MSI and EAC. We therefore examined MSI at BAT25 and BAT26 in a subset of microdissected targets (N=71). In this subset, MSI at BAT25 or BAT26 was detected in 4/43 microdissected targets histologically classified as HGD or EAC (data not shown). However, MSI in these markers was not detected in less severe BE histology (IM, IND, LGD), suggesting that MSI at these loci had little predictive value concerning disease progression in this subset. By contrast, the appearance of new alleles indicative of MSI was consistently observed in the microsatellite repeats of the 10 genomic loci in which LOH was also examined, both in less advanced (IM, IND, LGD) and more advanced histological classifications (HGD, EAC) (Table 2). To our knowledge, this is the first report of MSI related to BE in these microsatellites, which are composed of tetranucleotide repeats. The novel detection of MSI at these 10 loci in less severe histological classifications of BE (IM, IND, LGD) could be a result of MSI produced by mechanisms different than those associated with BAT25 and BAT26 mononucleotide repeats, which involve disruption of DNA repair (hMLH1/hMSH2) functions. In general, MSI at these 10 genomic loci slightly increased with increasingly severe histology (Table 16). More importantly, the addition of MSI to the assessment of ML helped to better stratify the difference in ML between less advanced (IM, IND, LGD) and more advanced (HGD, EAC) histological classifications of BE (FIG. 5).

We defined three levels of ML (no, low, and high ML), when MSI mutations and low and high clonality LOH mutations were assessed. These three levels were determined using the heterogeneous distribution of mutational load present in the population of targets with intestinal metaplasia histology (N=427). The levels were then applied to each histological classification to determine the proportion of targets captured in each level (Table 18). The three levels were stratified using the distribution of ML in intestinal metaplasia targets, because intestinal metaplasia histology was the most reliably classified histology amongst all three pathologist in the subset of microdissected targets analyzed here, which has also been observed by others (Table 17).

High, low, and no levels of mutational load captured relatively similar proportions of microdissected targets with each histology as compared to that of a past single cohort study 3. Importantly, microdissected targets with HGD (95%) or EAC (96%) consistently had high ML (Table 18) and about half of LGD (46%) histological targets had high ML in both studies. Although the presence of HGD and confirmed LGD are risk factors for progression to EAC, lack of pathologist agreement concerning LGD and indefinite for dysplasia histological classifications, as observed here and in other studies, suggests a need for additional, more objective clinical information when such diagnoses are encountered (Table 17). ML can provide information about genomic instability for these inconsistent histological classifications of BE.

Importantly, a proportion of non-dysplastic BE targets with intestinal metaplasia (8% high ML) and indefinite for dysplasia (16% high ML) histology had a similar ML as those with HGD and EAC histology (Table 18). Therefore, this portion of targets had molecular changes that are similar to those seen with high risk and severe disease (HGD, EAC), which is consistent with that observed in previous work concerning ML 3. High ML in less severe histological classifications of BE may be indicative of imminent morphological changes that have yet to become visible by histology. A relatively high load of molecular changes, which occurs in a fraction of microdissected targets with less advanced histology, may help to more objectively identify targets that are more likely to develop into advanced BE histology (HGD or EAC).

By contrast, mutations were not always present in microdissected targets with less severe histology (COL, IM, IND, LGD). The proportion of microdissected targets that lacked mutations (no ML) decreased with increasingly severe histology (Table 18), consistent with previous work describing ML. Importantly, lack of mutations (no ML) was not detected in any microdissected targets with HGD or EAC histology. Because the loci examined in this study are a survey of genomic sites relevant to Barrett's-associated EAC, the absence of clonally expanded LOH mutations and MSI mutations next to these 10 relevant genomic loci provides strong evidence that the histological targets examined did not have extensive genomic instability related to BE. Therefore, the lack of mutational load (no ML) in a portion of BE targets with less severe histology is likely indicative of benign biological processes. In addition, low levels of mutations (low ML) were present in columnar mucosa (COL), suggesting that the presence of a few mutations alone is not necessarily indicative of higher risk histological disease.

Our study is consistent with others describing genomic instability around TP53 and CDKN2A tumor suppressor genes, which has been associated with greater risk of BE histological progression to EAC. Similar to these studies, LOH in the microsatellite regions of TP53 and CDKN2A tumor suppressor genes were included in our panel. LOH mutations in these loci were found most frequently in microdissected targets with histological dysplasia (Table 16). However, consistent with previous work, many additional genomic loci also had LOH in dysplastic targets and targets with EAC, suggesting that all loci are relevant to progressive Barrett's disease. Furthermore, many genomic loci had LOH mutations in non-dysplastic targets (IM, indefinite for dysplasia) in comparable frequency to CDKN2A and TP53 associated mutations, suggesting that other genomic loci beyond those related to TP53 and CDKN2A are present at even early stages of BE. Similarly, MSI mutations at these 10 genomic loci occurred more often in dysplastic microdissected targets but were also present in non-dysplastic targets across nearly all loci.

While the strengths of this study have demonstrated that mutational load can provide an objective measure of the presence and extent of genomic instability amongst BE histological classifications, there are study limitations to consider. Limitations in this study include those inherent to studies correlating information to histological diagnoses. Due to variability in pathologist diagnoses, there is unavoidable variability in the histological classification used as the reference standard when correlating molecular results. However, when consensus histological classification was compared to ML in a subset of microdissected targets, the correlation between histological diagnosis and mutational load was still observed (data not shown), although only limited dysplastic histological targets were available for multiple pathologist review in this subset.

The results of this study support the use of mutational load assessments in conjunction with histological classification of BE to better manage patients. ML assesses the presence and extent of genomic instability, which has been associated with increased risk of progression to EAC 4. A portion of microdissected targets with non-dysplastic histological classifications shared a similar ML as those with higher risk disease (HGD) and even EAC. Given that EAC is associated with accumulated genomic instability, high ML in less severe histological diagnoses may be an indication of BE disease at higher risk of progression to EAC. Therefore, mutational load may help to better manage BE patients in early stages of disease and when histological diagnosis provides insufficient information. Incorporating assessments for ML in patient management may help to reduce health economic costs and increase patient quality of life by limiting unnecessary clinical interventions and frequent surveillance in patients destined for non-malignant disease and by allowing earlier and less morbid intervention in patients destined for malignancy.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or an limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges, which can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

Although the present invention has been described in considerable detail with reference to certain preferred embodiments thereof, other versions are possible. Therefore, the spirit and scope of the appended claims should not be limited to the description and the preferred versions contained within this specification.

What is claimed:

1. A method for treating subject with a high risk of disease progression from Barrett's metaplasia to esophageal adenocarcinoma, the method comprising:

determining mutational load as a predictor of the risk of disease progression from Barrett's metaplasia to esophageal adenocarcinoma in a subject, by:

amplifying DNA sequences in microsatellite regions 1p (CMM1, Lmyc), 3p (VHL, OGG1), 5q (MCC, APC), 9p (CDKN2A, CDKN2B), 10q (PTEN, MXI1), 17p (TP53), 17q (NME1), 18q (DCC), and 21q, 22q (NF2) from a biological specimen from the subject;

detecting mutations in the microsatellite regions of the amplified DNA sequences;

categorizing clonality of each mutation, wherein categorizing clonality of each mutation comprises assigning one of three categories selected from the group consisting of no clonality, low clonality and high clonality, wherein high clonality is assigned where loss of heterozygosity is present in greater than about 75% of DNA analyzed, low clonality is assigned where loss of heterozygosity is present in about 50% to about 75% of DNA analyzed; and no clonality is assigned where loss of heterozygosity is present in less than about 50% of DNA analyzed;

calculating a mutational load based on the sum of low and high clonality mutations; wherein DNA microsatellite instability at a single locus is defined as $0.75z_1$, and wherein DNA microsatellite instability at multiple loci is defined as $0.75z_1+0.5z_2$, wherein $z_1$ represent a single locus displaying DNA microsatellite instability and $z_2$ is the number of loci displaying DNA microsatellite instability greater than 1 locus; wherein the score for low clonality is $0.5x$, wherein x is the number of low clonality mutations and the score for high clonality is y, wherein y is the number of high clonality mutations; and wherein the overall mutational load is $y+0.5x+0.75z_1+0.5z_2$;

assigning the subject to a risk category to a high mutational load risk category when the subject has a mutational load greater than or equal to 1.75; and administering to the subject that is assigned to the high mutational load risk category at least one treatment modality selected from endoscopic mucosal resection, endoscopic submucosal dissection, a therapeutically effective amount of radiofrequency ablation, a therapeutically effective amount of cryoablation, or a therapeutically effective amount of photodynamic therapy.

2. The method of claim 1, wherein the subject is a human diagnosed with Barrett's esophagus.

3. The method of claim 1, wherein the biological specimen is a mucosal lining of the esophagus.

4. The method of claim 1, wherein amplifying DNA sequences comprises:

selecting a primer pair corresponding to a specific microsatellite region;

adding the primer pair to the DNA sequences;

and performing quantitative polymerase chain reaction on the DNA sequences with the primer.

5. The method of claim 1, wherein detecting mutations comprises determining the sequence of the amplified DNA and comparing the amplified DNA to a known wild type control sequence for the specific microsatellite region and identifying differences between the sequence of the amplified DNA and the known wild type control sequence.

6. The method of claim 1, wherein DNA microsatellite instability is determined by the presence of at least one of the shortening and lengthening of a DNA microsatellite region.

7. The method of claim 1, wherein the method is independent of a histological standard.

8. The method of claim 1, wherein the biological specimen is a biopsy sample, fine needle aspirate sample, a cytology sample, a frozen tissue simple, or a fixed tissue sample.

9. The method of claim 1, further comprising removing the biological specimen from the subject prior to the amplifying step.

* * * * *